US011033366B2

(12) United States Patent
Mozes et al.

(10) Patent No.: US 11,033,366 B2
(45) Date of Patent: Jun. 15, 2021

(54) INTERACTIVE GUIDANCE AND MANIPULATION DETECTION ARRANGEMENTS FOR A SURGICAL ROBOTIC SYSTEM, AND ASSOCIATED METHOD

(71) Applicant: NEOCIS INC., Miami, FL (US)

(72) Inventors: Alon Mozes, Miami Beach, FL (US); Juan Salcedo, Miami, FL (US); William McMahan, Miami, FL (US); Ryan Anderson, Aventura, FL (US); Sarvagya Vaish, Miami, FL (US); David Cole, Bay Harbor Islands, FL (US)

(73) Assignee: NEOCIS INC., Miami, FL (US)

( * ) Notice: Subject to any disclaimer, the term of this patent is extended or adjusted under 35 U.S.C. 154(b) by 860 days.

(21) Appl. No.: 15/656,767

(22) Filed: Jul. 21, 2017

(65) Prior Publication Data
US 2017/0319302 A1 Nov. 9, 2017

Related U.S. Application Data

(63) Continuation of application No. PCT/US2016/014306, filed on Jan. 21, 2016.
(Continued)

(51) Int. Cl.
*A61C 8/00* (2006.01)
*A61C 1/08* (2006.01)
(Continued)

(52) U.S. Cl.
CPC ............ *A61C 8/0089* (2013.01); *A61B 34/20* (2016.02); *A61B 34/25* (2016.02); *A61B 34/30* (2016.02);
(Continued)

(58) Field of Classification Search
CPC . A61C 8/0089; A61C 1/084; A61C 2204/002; A61B 34/20; A61B 34/25;
(Continued)

(56) References Cited

U.S. PATENT DOCUMENTS

| 6,640,128 B2 * | 10/2003 | Vilsmeier | A61C 1/084 |
| | | | 433/215 |
| 8,808,000 B2 | 8/2014 | Salcedo et al. | |

(Continued)

FOREIGN PATENT DOCUMENTS

WO WO-2011091382 A1 * 7/2011 ............... A61B 6/14

*Primary Examiner* — Nicholas D Lucchesi
(74) *Attorney, Agent, or Firm* — Womble Bond Dickinson (US) LLP

(57) ABSTRACT

Dental implantation systems and methods are provided, including a system comprising a patient-interacting device having an instrument for preparing a site within a patient's mouth for a dental implant. A guiding device in communication with a fiducial marker engaged with the patient's mouth receives the patient-interacting device, and guides the instrument, relative to the fiducial marker, in conjunction with user manipulation of the patient-interacting device. A controller device including a processor is in communication with the guiding device, and directs the patient-interacting device via the guiding device to prepare the site to receive the dental implant. An engagement sensor is operably engaged with the patient-interacting device and communicates with the controller device. The controller device is responsive to sensed disengagement between the patient-interacting device and the user to direct the guiding device to maintain the patient-interacting device at a minimum vertical disposition. Associated systems and methods are also provided.

42 Claims, 7 Drawing Sheets

Related U.S. Application Data

Figure 1:
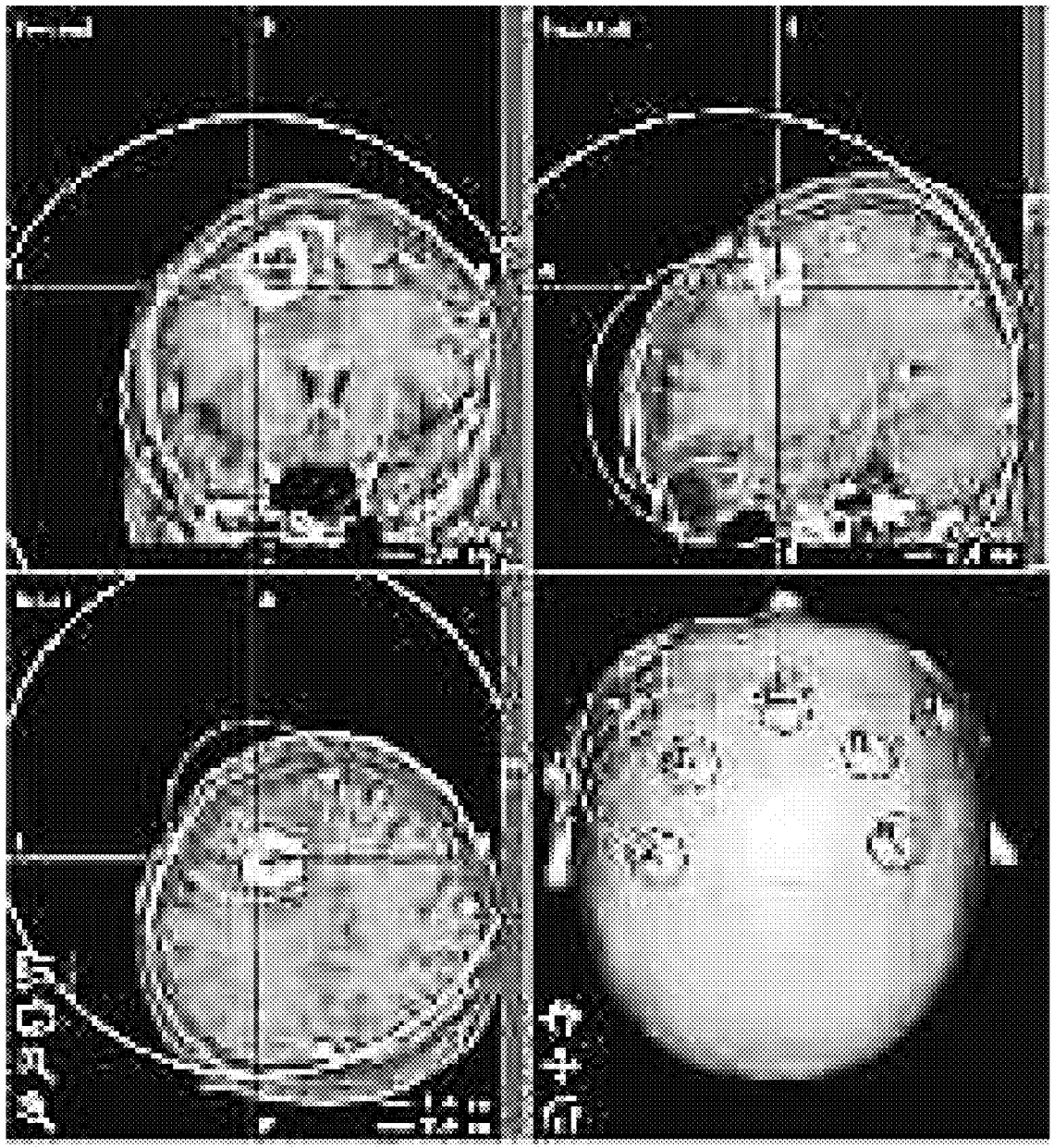

(60) Provisional application No. 62/106,343, filed on Jan. 22, 2015.

(51) Int. Cl.
    *A61B 90/50*     (2016.01)
    *A61B 34/00*     (2016.01)
    *G16H 20/40*     (2018.01)
    *G16H 30/20*     (2018.01)
    *A61B 34/20*     (2016.01)
    *A61B 34/30*     (2016.01)
    *A61B 90/00*     (2016.01)

(52) U.S. Cl.
    CPC .............. *A61B 34/76* (2016.02); *A61B 90/36* (2016.02); *A61B 90/50* (2016.02); *A61C 1/084* (2013.01); *G16H 20/40* (2018.01); *G16H 30/20* (2018.01); *A61B 2034/2046* (2016.02); *A61B 2034/2055* (2016.02); *A61B 2034/2068* (2016.02); *A61B 2034/254* (2016.02); *A61B 2090/064* (2016.02); *A61B 2090/363* (2016.02); *A61B 2090/3966* (2016.02); *A61B 2090/3991* (2016.02); *A61C 2204/002* (2013.01)

(58) Field of Classification Search
    CPC ......... A61B 34/76; A61B 90/36; A61B 90/50; A61B 2034/2046; A61B 2034/2055; A61B 2034/2068; A61B 2034/254; A61B 2090/064; A61B 2090/363; A61B 2090/3966; A61B 2090/3991; G06F 19/321; G06F 19/3481
See application file for complete search history.

(56) References Cited

U.S. PATENT DOCUMENTS

| | | | |
|---|---|---|---|
| 8,983,813 B2* | 3/2015 | Miles | A61F 2/30942 703/2 |
| 9,411,910 B2* | 8/2016 | Methot | B33Y 80/00 |
| 9,468,504 B2* | 10/2016 | Jung | A61C 1/082 |
| 9,962,234 B2* | 5/2018 | Chodorow | A61C 19/02 |
| 10,350,036 B2* | 7/2019 | Suttin | A61B 6/032 |
| 10,426,572 B2* | 10/2019 | Tahmasebi | A61C 1/082 |
| 2005/0116673 A1* | 6/2005 | Carl | A61B 17/1626 318/432 |
| 2006/0142657 A1* | 6/2006 | Quaid | A61B 17/1764 600/424 |
| 2009/0253095 A1* | 10/2009 | Salcedo | A61C 5/90 433/75 |
| 2013/0017507 A1 | 1/2013 | Moffson et al. | |
| 2013/0261433 A1 | 10/2013 | Daon | |
| 2014/0027289 A1 | 1/2014 | Lee et al. | |
| 2014/0272789 A1* | 9/2014 | Mozes | A61B 6/14 433/173 |
| 2015/0140507 A1* | 5/2015 | Moffson | A61B 90/39 433/75 |
| 2015/0202739 A1* | 7/2015 | Lee | B24C 1/06 205/50 |

* cited by examiner

INTERACTIVE GUIDANCE AND MANIPULATION DETECTION ARRANGEMENTS FOR A SURGICAL ROBOTIC SYSTEM, AND ASSOCIATED METHOD

CROSS-REFERENCE TO RELATED APPLICATIONS

This application is a continuation of International Application No. PCT/US2016/014306, filed Jan. 21, 2016, which International Application was published by the International Bureau in English on Jul. 28, 2016, claims priority to U.S. Provisional Application No. 62/106,343, filed Jan. 22, 2015, all which are incorporated herein by reference in their entirety and for all purposes.

BACKGROUND

Field of the Disclosure

The present application relates to surgical robots and associated guidance systems and, more particularly, to a guided surgical robot system used, for example, in dental surgery, wherein the system is also configured to detect and be responsive to manipulation by/disengagement from a user thereof, as well as to interactively track the guided surgical instrument during the surgical procedure.

Description of Related Art

A dental implant procedure generally involves several aspects: making the diagnosis, planning the position of the implant, surgically milling the anatomy and placing the implant (i.e., an anchoring post), and then attaching the abutment and crown (i.e., prosthetic tooth/teeth). In some instance, such a procedure may be automated, for example, via a robotic surgical system. Some surgical systems, such as dental implantation surgical systems, may implement planning of the surgical procedure based on non-invasive imaging of the planned surgical site (i.e., via a CT scan). The result of the plan, namely the collected image(s) of the surgical site or patient anatomy, can thus be used, for example, for diagnosis, for manufacturing a drill guide, or for guiding haptic or autonomous robotic systems.

Some haptic robotic systems are configured to interact with the user/surgeon by responding to the forces applied by the user/surgeon during the procedure. For example, the surgical instrument (i.e., drill) may be generally arranged to be mounted on or in association with suitable force sensors. In instances of haptic robotic systems implementing an arrangement of one or more robotic arms to which the surgical instrument is mounted, "gravity compensation" may sometimes be required to counteract or compensate for the force of gravity on the arm(s) (i.e., in order to make the arm(s)/surgical instrument feel weightless to the user/surgeon). However, since there is an element of interactivity with the user, such a system may sometimes have difficulty discerning between the various forces involved and acting upon the arm(s)/surgical instrument such as, for example force applied by the user, any drift of the force sensor which may result in the detection of "phantom" forces, the force of gravity, or the force of resistance (i.e., from the drill drilling into the patient's bone structure). As a result, the counteracting or compensating force may not accurately correlate to the actual forces involved and acting upon the arm(s)/surgical instrument.

As such, it may be desirable to provide a surgical robotic system and method having the capability of determining whether the user was actively engaging with the system, so as to better respond to the actual forces involved and acting upon the arm(s)/surgical instrument. Such capabilities may also desirably facilitate safety of the system, for example, by having the capability of detecting movement of the arm(s)/surgical instrument in stances where the user is not actively engaged with or holding the surgical instrument.

In other instances, some navigated and/or guided medical devices may provide feedback to the user, for example, via software-enabled visualizations, physical haptics, and/or audio cues, though such forms of feedback may not necessarily intuitive for the user. For example, some existing feedback methods may implement a "flight simulator" style of visual guide (see, e.g., FIG. 1) that may simultaneously display circles/crosshairs in relation to a target site on a number of two-dimensional images, which requires the user to manipulate the surgical instrument so as to line up the circles/crosshairs with the target on each image in the array of 2D images: Manipulating the surgical instrument in such an environment may not necessarily be intuitive to the user (surgeon), perhaps even with significant experience using the system.

As such, it may be also be desirable to provide a surgical robotic system and method having feedback capabilities that more intuitively guide the user in effectively and efficiently manipulating the surgical instrument during the surgical procedure. Such capabilities may also desirably facilitate safety of the system, for example, by reducing "trial and error" manipulation of the surgical instrument by the user, particularly if the user is not significantly experienced with the system.

SUMMARY OF THE DISCLOSURE

The above and other needs are met by aspects of the present disclosure which, in one particular aspect, provides a dental implantation system, comprising a patient-interacting device having an instrument adapted to at least interact with and prepare a site within a mouth of a patient for receiving a dental implant. A guiding device is in communication with a fiducial marker adapted to be engaged with the mouth of the patient, wherein the guiding device is configured to receive the patient-interacting device. The guiding device is also configured to guide the instrument of the patient-interacting device, relative to the fiducial marker, in conjunction with manipulation of the patient-interacting device by a user. A controller device includes a processor, and is configured to be in communication with the guiding device. The controller device is also configured to direct the patient-interacting device via the guiding device to prepare the site to receive the dental implant. An engagement sensor is operably engaged with the patient-interacting device, and is configured to be in communication with the controller device. The engagement sensor is further responsive to disengagement between the patient-interacting device and the user to direct the guiding device to at least maintain the patient-interacting device at a minimum vertical disposition.

Another aspect provides a dental implantation method, comprising guiding an instrument of a patient-interacting device, via a guiding device and relative to a fiducial marker adapted to be engaged with a mouth of a patient, in conjunction with manipulation of the patient-interacting device by a user, wherein the patient-interacting device is received by the guiding device, and the instrument is configured to interact with and prepare the site within the mouth of the patient for receiving a dental implant. The patient-interacting device is guided, via the guiding device, to prepare the site to receive the dental implant, via a controller device including a processor, wherein the controller device is configured to be in communication with the guiding device. The guiding device is directed to at least maintain the patient-interacting device at a minimum vertical disposition, via the controller device, in response to disengagement between the patient-interacting device and the user, as determined by an engagement sensor operably engaged with the patient-interacting device and configured to be in communication with the controller device.

Yet another aspect provides a dental implantation system, comprising a patient-interacting device having an instrument adapted to at least interact with and prepare a site within a mouth of a patient for receiving a dental implant, and a guiding device in communication with a fiducial marker adapted to be engaged with the mouth of the patient. The guiding device is configured to receive the patient-interacting device, and to guide the instrument of the patient-interacting device, relative to the fiducial marker, in conjunction with manipulation of the patient-interacting device by a user. A display device is configured to display a real-time representation of the instrument of the patient-interacting device, in relation to a representation of the mouth of the patient, during manipulation of the patient-interacting device by the user. A controller device, including a processor, is configured to be in communication with the guiding device and the display device. The controller device is configured to direct the patient-interacting device, via the guiding device and according to a virtual implantation plan, to prepare the site to receive the dental implant, and to direct tactile feedback to the user, via the patient-interacting device, if the instrument manipulated by the user deviates from the virtual implantation plan. The controller device is further configured to one of direct the display device to display the real-time representation of the instrument in relation to a virtual representation of the instrument of the patient-interacting device manipulated in accordance with the virtual implantation plan, direct an audio device in communication therewith to emit a selected audio signal indicative of the patient-interacting device manipulated in accordance with the virtual implantation plan, and direct the guiding device to provide a selected resistance to manipulation of the patient-interacting device in accordance with the virtual implantation plan.

Still another aspect provides a dental implantation method, comprising guiding an instrument of a patient-interacting device, via a guiding device and relative to a fiducial marker adapted to be engaged with a mouth of a patient, in conjunction with manipulation of the patient-interacting device by a user, wherein the patient-interacting device is received by the guiding device, and the instrument is configured to interact with and prepare the site within the mouth of the patient for receiving a dental implant; displaying a real-time representation of the instrument of the patient-interacting device on a display device, in relation to a representation of the mouth of the patient, during manipulation of the patient-interacting device by the user; directing the patient-interacting device, via the guiding device and according to a dental implantation plan, to prepare the site to receive the dental implant, via a controller device including a processor, wherein the controller device is configured to be in communication with the guiding device and the display device; directing tactile feedback to the user, via the patient-interacting device, if the instrument manipulated by the user deviates from the virtual implantation plan; and one of directing the display device, via the controller device, to display the real-time representation of the instrument in relation to a virtual representation of the instrument of the patient-interacting device manipulated in accordance with the virtual implantation plan; directing an audio device, via the controller device in communication therewith, to emit a selected audio signal indicative of the patient-interacting device manipulated in accordance with the virtual implantation plan; and directing the guiding device, via the controller device, to provide a selected resistance to manipulation of the patient-interacting device in accordance with the virtual implantation plan.

The present disclosure thus includes, without limitation, the following example embodiments:

Example Embodiment 1

A dental implantation system, wherein such a system comprises a patient-interacting device having an instrument adapted to at least interact with and prepare a site within a mouth of a patient for receiving a dental implant; a guiding device in communication with a fiducial marker adapted to be engaged with the mouth of the patient, wherein the guiding device is configured to receive the patient-interacting device, and to guide the instrument of the patient-interacting device, relative to the fiducial marker, in conjunction with manipulation of the patient-interacting device by a user; a controller device including a processor, wherein the controller device is configured to be in communication with the guiding device, and to direct the patient-interacting device via the guiding device to prepare the site to receive the dental implant; and an engagement sensor operably engaged with the patient-interacting device, and configured to be in communication with the controller device, the engagement sensor being configured to sense disengagement between the patient-interacting device and the user and to communicate the disengagement to the controller device, the controller device being responsive to the sensed disengagement to direct the guiding device to at least maintain the patient-interacting device at a minimum vertical disposition.

Example Embodiment 2

The system of any preceding or subsequent example embodiment, or combinations thereof, wherein the engagement sensor is further configured to be responsive to disengagement between the patient-interacting device and the user to direct the guiding device to maintain the patient-interacting device at one of a lateral disposition and a rotational orientation.

Example Embodiment 3

The system of any preceding or subsequent example embodiment, or combinations thereof, wherein the engagement sensor is further configured to be responsive to engagement between the patient-interacting device and the user to actuate the guiding device to guide at least the instrument of the patient-interacting device, relative to the fiducial marker.

Example Embodiment 4

The system of any preceding or subsequent example embodiment, or combinations thereof, wherein the engagement sensor is further configured to be responsive to engagement between the patient-interacting device and the user to at least permit the instrument to be actuated.

Example Embodiment 5

The system of any preceding or subsequent example embodiment, or combinations thereof, wherein the engagement sensor is further configured to be responsive to engagement between the patient-interacting device and the user to direct the controller device to actuate a virtual implantation plan for guiding at least the instrument of the patient-interacting device.

Example Embodiment 6

The system of any preceding or subsequent example embodiment, or combinations thereof, wherein the engagement sensor comprises one of a touch-sensitive actuator, a pressure-sensitive actuator, an optical actuator, and an acoustic actuator, associated with the patient-interacting device.

Example Embodiment 7

The system of any preceding or subsequent example embodiment, or combinations thereof, wherein at least one of the engagement sensor and the fiducial marker is configured to be in communication with the controller device via one of an electrical communication system, a mechanical communication system, an electromechanical communication system, an optical communication system, and combinations thereof.

Example Embodiment 8

The system of any preceding or subsequent example embodiment, or combinations thereof, wherein at least one of the engagement sensor and the fiducial marker is configured to be in communication with the controller device via one of wireless communication system and a wired communication system.

Example Embodiment 9

The system of any preceding or subsequent example embodiment, or combinations thereof, further comprising at least one force sensor operably engaged with at least one of the guiding device and the patient-interacting device, wherein the at least one force sensor is configured to measure a force acting on the patient-interacting device, and to communicate the measured force to the controller device.

Example Embodiment 10

The system of any preceding or subsequent example embodiment, or combinations thereof, wherein the controller device is responsive to disengagement from the engagement sensor by the user to zero the measured force from the at least one force sensor.

Example Embodiment 11

The system of any preceding or subsequent example embodiment, or combinations thereof, wherein the controller device is configured to execute a virtual implantation plan for the site within the mouth of the patient, and to direct the guiding device according to the virtual implantation plan, in response to engagement of the engagement sensor by the user.

Example Embodiment 12

The system of any preceding or subsequent example embodiment, or combinations thereof, wherein the controller device is configured to direct tactile feedback to the user, via the patient-interacting device, if the instrument manipulated by the user deviates from the virtual implantation plan.

Example Embodiment 13

The system of any preceding or subsequent example embodiment, or combinations thereof, wherein the controller device is configured to direct at least one of audio feedback and visual feedback to the user, via at least one of the controller device and the patient-interacting device, if the instrument manipulated by the user deviates from the virtual implantation plan.

Example Embodiment 14

The system of any preceding or subsequent example embodiment, or combinations thereof, further comprising a display device configured to display a real-time representation of at least the instrument of the patient-interacting device, in relation to a representation of the mouth of the patient, during engagement with and manipulation of the patient-interacting device by the user.

Example Embodiment 15

The system of any preceding or subsequent example embodiment, or combinations thereof, wherein the controller device is configured to be in communication with the guidance device and the display device, and wherein the controller device is configured to monitor manipulation of at least the instrument of the patient-interacting device in relation to the mouth of the patient, at least partially via the guidance device, and to direct information associated therewith to the display device.

Example Embodiment 16

A dental implantation method, wherein such a method comprises guiding an instrument of a patient-interacting device, via a guiding device and relative to a fiducial marker adapted to be engaged with a mouth of a patient, in conjunction with manipulation of the patient-interacting device by a user, wherein the patient-interacting device is received by the guiding device, and the instrument is configured to interact with and prepare the site within the mouth of the patient for receiving a dental implant; directing the patient-interacting device, via the guiding device, to prepare the site to receive the dental implant, via a controller device including a processor, wherein the controller device is configured to be in communication with the guiding device; and directing the guiding device to at least maintain the patient-interacting device at a minimum vertical disposition, via the controller device, in response to disengagement between the patient-interacting device and the user determined by an engagement sensor operably engaged with the patient-interacting device and configured to be in communication with the controller device.

Example Embodiment 17

The method of any preceding or subsequent example embodiment, or combinations thereof, further comprising directing the guiding device to maintain the patient-interacting device at one of a lateral disposition and a rotational orientation, in response to disengagement between the patient-interacting device and the user determined by the engagement sensor.

Example Embodiment 18

The method of any preceding or subsequent example embodiment, or combinations thereof, further comprising actuating the guiding device to guide at least the instrument of the patient-interacting device, relative to the fiducial marker, in response to engagement between the patient-interacting device and the user determined by the engagement sensor.

Example Embodiment 19

The method of any preceding or subsequent example embodiment, or combinations thereof, further comprising at least permitting the instrument to be actuated, in response to engagement between the patient-interacting device and the user determined by the engagement sensor.

Example Embodiment 20

The method of any preceding or subsequent example embodiment, or combinations thereof, further comprising directing the controller device to actuate a virtual implantation plan for guiding at least the instrument of the patient-interacting device, in response to engagement between the patient-interacting device and the user determined by the engagement sensor.

Example Embodiment 21

The method of any preceding or subsequent example embodiment, or combinations thereof, wherein directing the guiding device in response to disengagement between the patient-interacting device and the user determined by an engagement sensor operably engaged with the patient-interacting device, further comprises directing the guiding device in response to disengagement between the patient-interacting device and the user determined by one of a touch-sensitive actuator, a pressure-sensitive actuator, an optical actuator, and an acoustic actuator, associated with the patient-interacting device.

Example Embodiment 22

The method of any preceding or subsequent example embodiment, or combinations thereof, further comprising communicating between at least one of the engagement sensor and the fiducial marker, and the controller device, via one of an electrical communication system, a mechanical communication system, an electromechanical communication system, an optical communication system, and combinations thereof.

Example Embodiment 23

The method of any preceding or subsequent example embodiment, or combinations thereof, further comprising communicating between at least one of the engagement sensor and the fiducial marker, and the controller device, via one of wireless communication system and a wired communication system.

Example Embodiment 24

The method of any preceding or subsequent example embodiment, or combinations thereof, further comprising measuring a force acting on the patient-interacting device, and communicating the measured force to the controller device, wherein the measured force is determined by at least one force sensor operably engaged with at least one of the guiding device and the patient-interacting device.

Example Embodiment 25

The method of any preceding or subsequent example embodiment, or combinations thereof, further comprising zeroing the measured force from the at least one force sensor, via the controller device, in response to disengagement from the engagement sensor by the user.

Example Embodiment 26

The method of any preceding or subsequent example embodiment, or combinations thereof, further comprising executing a virtual implantation plan for the site within the mouth of the patient, and directing the guiding device according to the virtual implantation plan, via the controller device, in response to engagement of the engagement sensor by the user.

Example Embodiment 27

The method of any preceding or subsequent example embodiment, or combinations thereof, further comprising directing tactile feedback to the user, via the patient-interacting device, if the instrument manipulated by the user deviates from the virtual implantation plan.

Example Embodiment 28

The method of any preceding or subsequent example embodiment, or combinations thereof, further comprising directing at least one of audio feedback and visual feedback to the user, via at least one of the controller device and the patient-interacting device, if the instrument manipulated by the user deviates from the virtual implantation plan.

Example Embodiment 29

The method of any preceding or subsequent example embodiment, or combinations thereof, further comprising displaying, via a display device, a real-time representation of at least the instrument of the patient-interacting device, in relation to a representation of the mouth of the patient, during engagement with and manipulation of the patient-interacting device by the user.

Example Embodiment 30

The method of any preceding or subsequent example embodiment, or combinations thereof, further comprising monitoring manipulation of at least the instrument of the patient-interacting device in relation to the mouth of the patient, at least partially via the guidance device and the controller device, and directing information associated therewith to the display device.

Example Embodiment 31

A dental implantation system, wherein such a system comprises a patient-interacting device having an instrument adapted to at least interact with and prepare a site within a mouth of a patient for receiving a dental implant; a guiding device in communication with a fiducial marker adapted to be engaged with the mouth of the patient, wherein the guiding device is configured to receive the patient-interacting device, and to guide the instrument of the patient-interacting device, relative to the fiducial marker, in conjunction with manipulation of the patient-interacting device by a user; a display device configured to display a real-time representation of the instrument of the patient-interacting device, in relation to a representation of the mouth of the patient, during manipulation of the patient-interacting device by the user; and a controller device including a processor, and configured to be in communication with the guiding device and the display device, wherein the controller device is configured to direct the patient-interacting device, via the guiding device and according to a virtual implantation plan, to prepare the site to receive the dental implant, and to direct tactile feedback to the user, via the patient-interacting device, if the instrument manipulated by the user deviates from the virtual implantation plan, and wherein the controller device is further configured to direct the display device to display the real-time representation of the instrument in relation to a virtual representation of the instrument of the patient-interacting device manipulated in accordance with the virtual implantation plan, and direct an audio device in communication therewith to emit a selected audio signal indicative of the instrument of the patient-interacting device in the real-time representation of the instrument being manipulated in accordance with the virtual implantation plan, or direct the guiding device to provide a selected resistance to manipulation of the instrument of the patient-interacting device in accordance with the real-time representation of the instrument in relation to the virtual implantation plan.

Example Embodiment 32

The system of any preceding or subsequent example embodiment, or combinations thereof, wherein the controller device is further configured to direct the display device to display an animation of the virtual representation of the instrument of the patient-interacting device manipulated in accordance with the virtual implantation plan, and wherein the animation originates from a disposition of the real-time representation of the instrument of the patient-interacting device.

Example Embodiment 33

The system of any preceding or subsequent example embodiment, or combinations thereof, wherein the controller device is further configured to direct the display device to display a progress indicia originating from the disposition of the real-time representation of the instrument of the patient-interacting device, and progressing in relation to a required manipulation of the patient-interacting device for the instrument to be in accordance with the virtual implantation plan.

Example Embodiment 34

The system of any preceding or subsequent example embodiment, or combinations thereof, wherein the progress indicia comprises one of a distance originating from the disposition of the real-time representation of the instrument to a disposition of the instrument in accordance with the virtual implantation plan, and a degree of rotation originating from the disposition of the real-time representation of the instrument to a disposition of the instrument in accordance with the virtual implantation plan.

Example Embodiment 35

The system of any preceding or subsequent example embodiment, or combinations thereof, wherein the audio device is configured to emit a selected audio signal, the selected audio signal increasing in frequency from the disposition of the real-time representation of the instrument toward a disposition of the instrument in accordance with the virtual implantation plan.

Example Embodiment 36

The system of any preceding or subsequent example embodiment, or combinations thereof, wherein the guiding device is configured to provide a low resistance to manipulation of the patient-interacting device on one of manipulation of the patient-interacting device to move the instrument along a pathway in accordance with the virtual implantation plan, and manipulation of the patient-interacting device to rotate the instrument to a degree of rotation in accordance with the virtual implantation plan, and wherein the guiding device is further configured to provide a high resistance to manipulation of the patient-interacting device if one of the movement of the instrument along the pathway and rotation of the instrument deviates from the virtual implantation plan.

Example Embodiment 37

A dental implantation method, wherein such a method comprises guiding an instrument of a patient-interacting device, via a guiding device and relative to a fiducial marker adapted to be engaged with a mouth of a patient, in conjunction with manipulation of the patient-interacting device by a user, wherein the patient-interacting device is received by the guiding device, and the instrument is configured to interact with and prepare the site within the mouth of the patient for receiving a dental implant; displaying a real-time representation of the instrument of the patient-interacting device on a display device, in relation to a representation of the mouth of the patient, during manipulation of the patient-interacting device by the user; directing the patient-interacting device, via the guiding device and according to a dental implantation plan, to prepare the site to receive the dental implant, via a controller device including a processor, wherein the controller device is configured to be in communication with the guiding device and the display device; directing tactile feedback to the user, via the patient-interacting device, if the instrument manipulated by the user deviates from the virtual implantation plan; and one of directing the display device, via the controller device, to display the real-time representation of the instrument in relation to a virtual representation of the instrument of the patient-interacting device manipulated in accordance with the virtual implantation plan; directing an audio device, via the controller device in communication therewith, to emit a selected audio signal indicative of the patient-interacting device manipulated in accordance with the virtual implantation plan; and directing the guiding device, via the controller device, to provide a selected resistance to manipulation of the patient-interacting device in accordance with the virtual implantation plan.

Example Embodiment 38

The method of any preceding or subsequent example embodiment, or combinations thereof, wherein directing the display device, via the controller device, to display the real-time representation of the instrument, further comprises directing the display device, via the controller device, to display an animation of the virtual representation of the instrument of the patient-interacting device manipulated in accordance with the virtual implantation plan, wherein the animation originates from a disposition of the real-time representation of the instrument of the patient-interacting device.

Example Embodiment 39

The method of any preceding or subsequent example embodiment, or combinations thereof, further comprising directing the display device, via the controller device, to display a progress indicia originating from the disposition of the real-time representation of the instrument of the patient-interacting device, and progressing in relation to a required manipulation of the patient-interacting device for the instrument to be in accordance with the virtual implantation plan.

Example Embodiment 40

The method of any preceding or subsequent example embodiment, or combinations thereof, wherein directing the display device, via the controller device, to display a progress indicia, further comprises, directing the display device, via the controller device, to display a progress indicia comprising one of a distance originating from the disposition of the real-time representation of the instrument to a disposition of the instrument in accordance with the virtual implantation plan, and a degree of rotation originating from the disposition of the real-time representation of the instrument to a disposition of the instrument in accordance with the virtual implantation plan.

Example Embodiment 41

The method of any preceding or subsequent example embodiment, or combinations thereof, wherein directing an audio device, via the controller device in communication therewith, to emit a selected audio signal, further comprises directing an audio device, via the controller device in communication therewith, to emit a selected audio signal increasing in frequency from the disposition of the real-time representation of the instrument toward a disposition of the instrument in accordance with the virtual implantation plan.

Example Embodiment 38

The method of any preceding or subsequent example embodiment, or combinations thereof, wherein directing the guiding device, via the controller device, to provide a selected resistance to manipulation of the patient-interacting device, further comprises directing the guiding device, via the controller device, to provide a low resistance to manipulation of the patient-interacting device on one of manipulation of the patient-interacting device to move the instrument along a pathway in accordance with the virtual implantation plan, and manipulation of the patient-interacting device to rotate the instrument to a degree of rotation in accordance with the virtual implantation plan, and directing the guiding device, via the controller device, to provide a high resistance to manipulation of the patient-interacting device if one of the movement of the instrument along the pathway and rotation of the instrument deviates from the virtual implantation plan.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 2A:
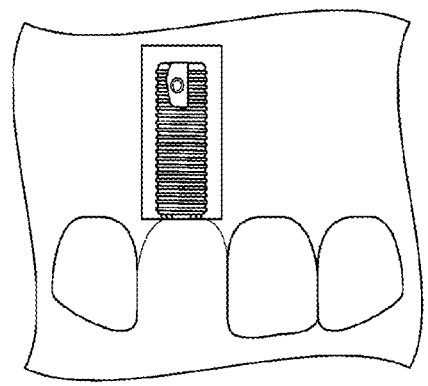
Figure 2B:
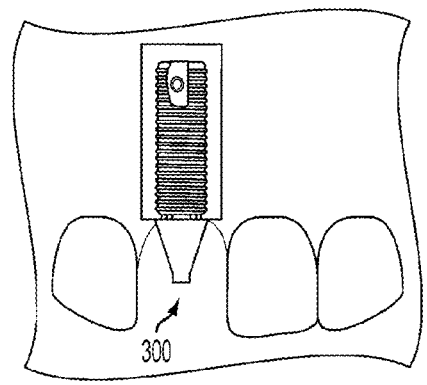
Figure 2C:
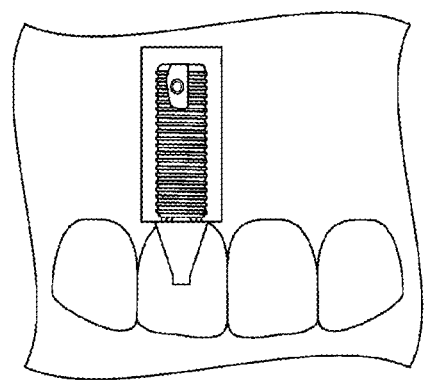
Figure 3:
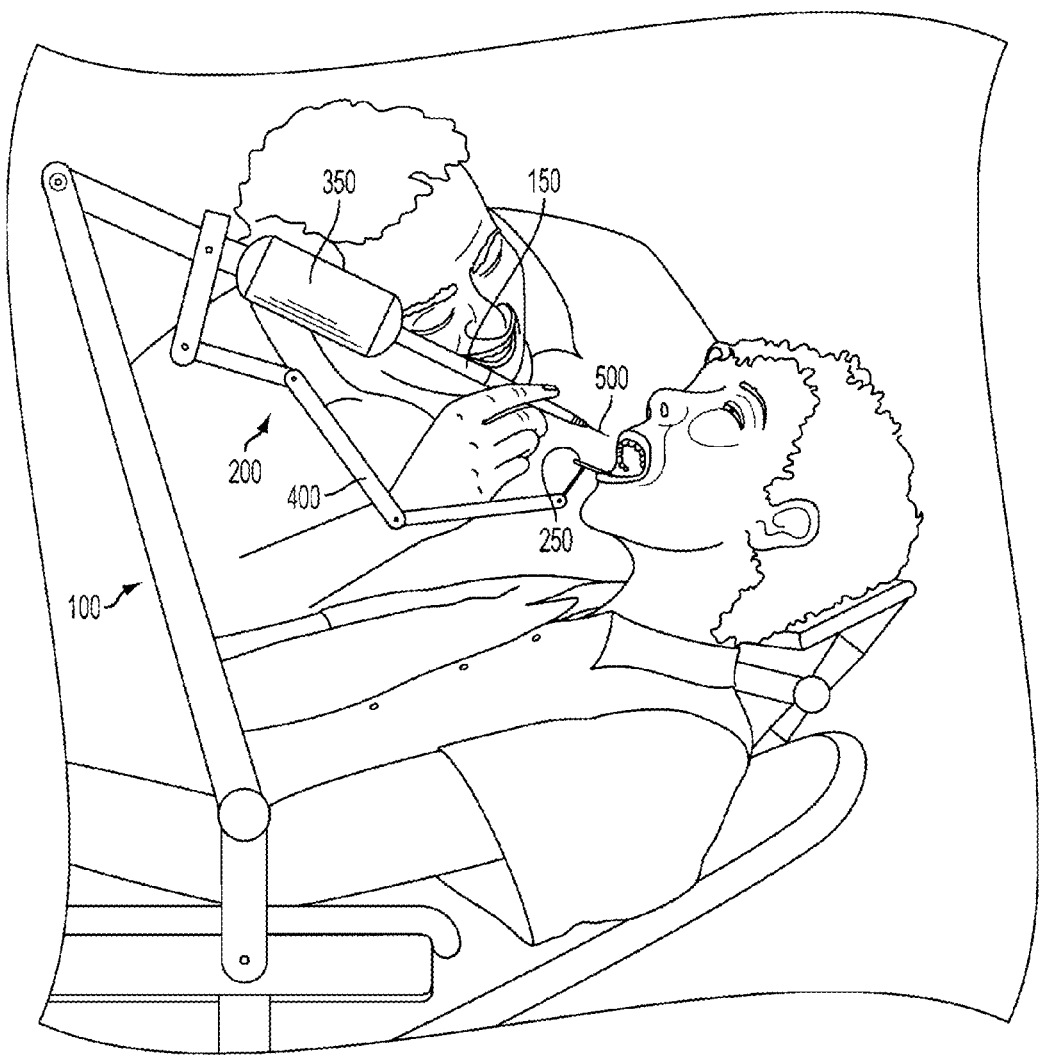
Figure 4:
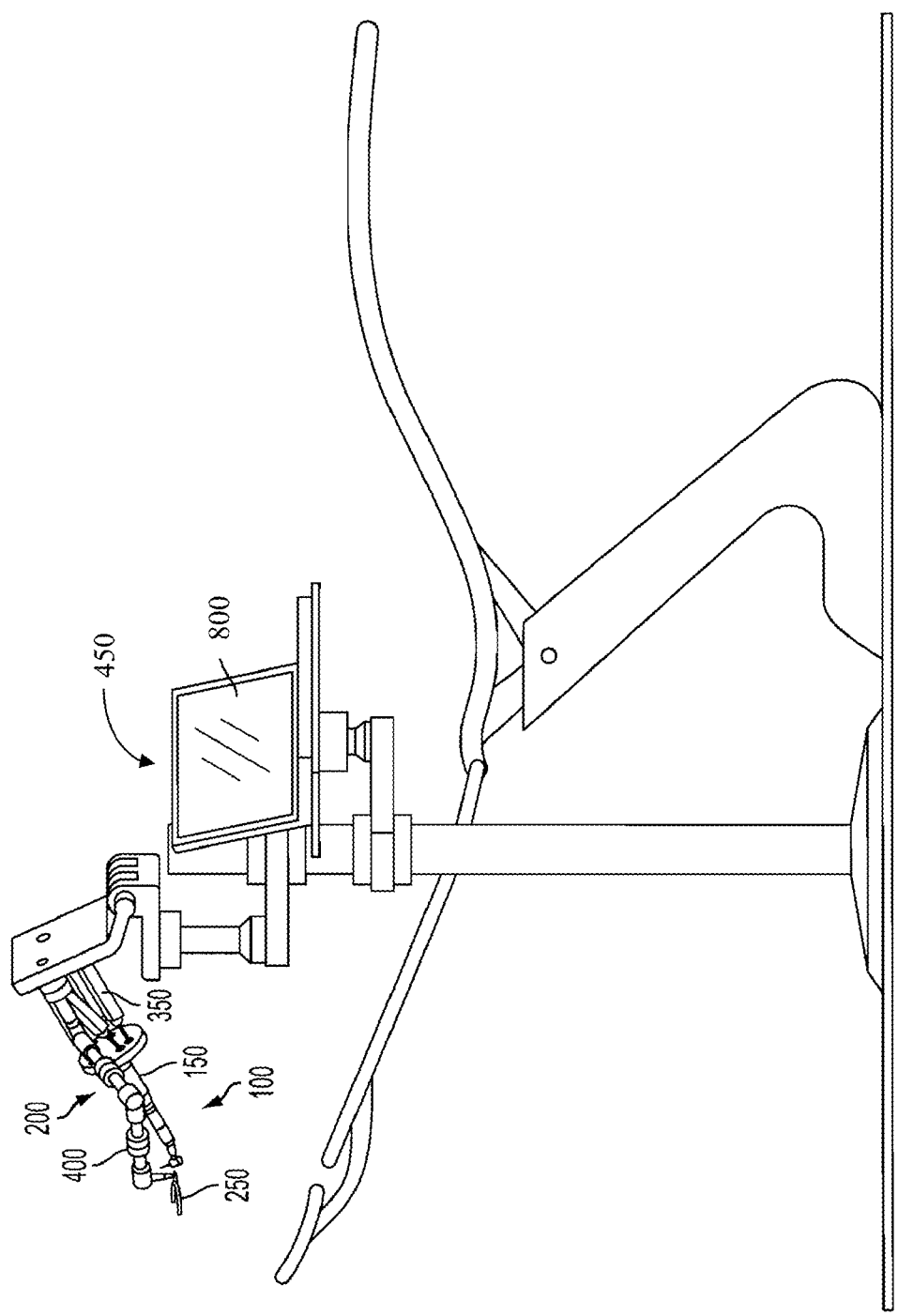
Figure 5:
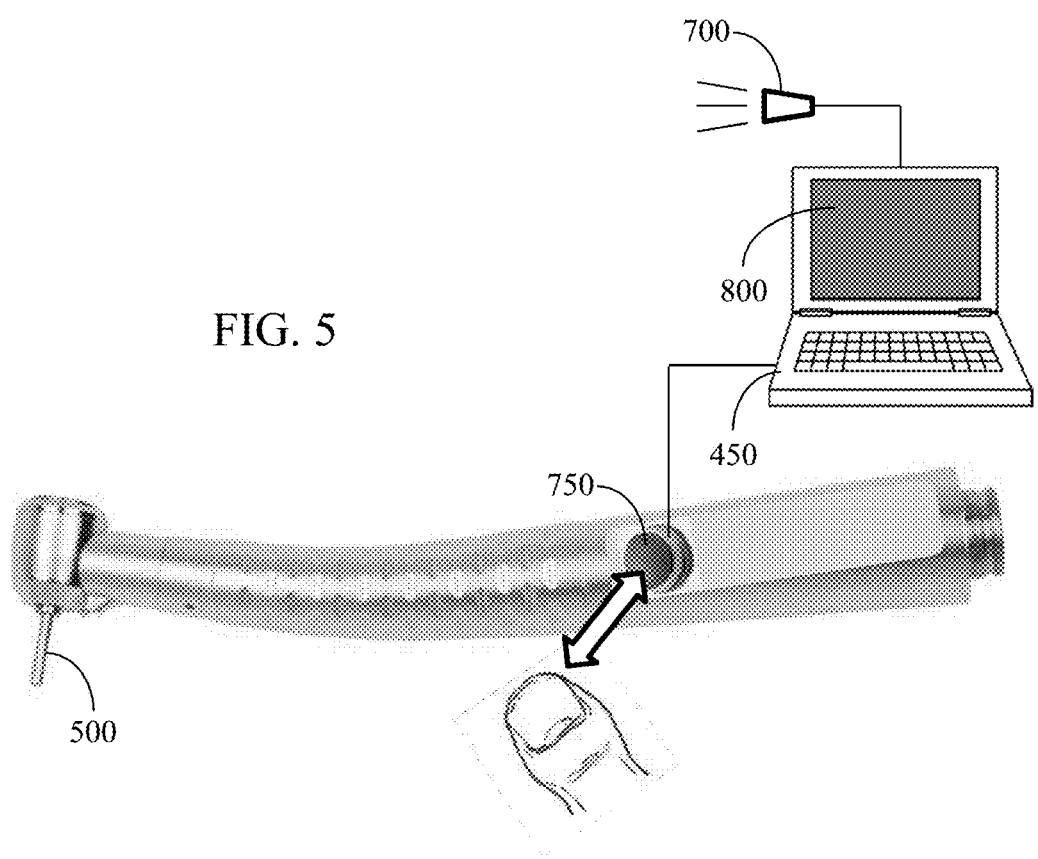
Figure 6:
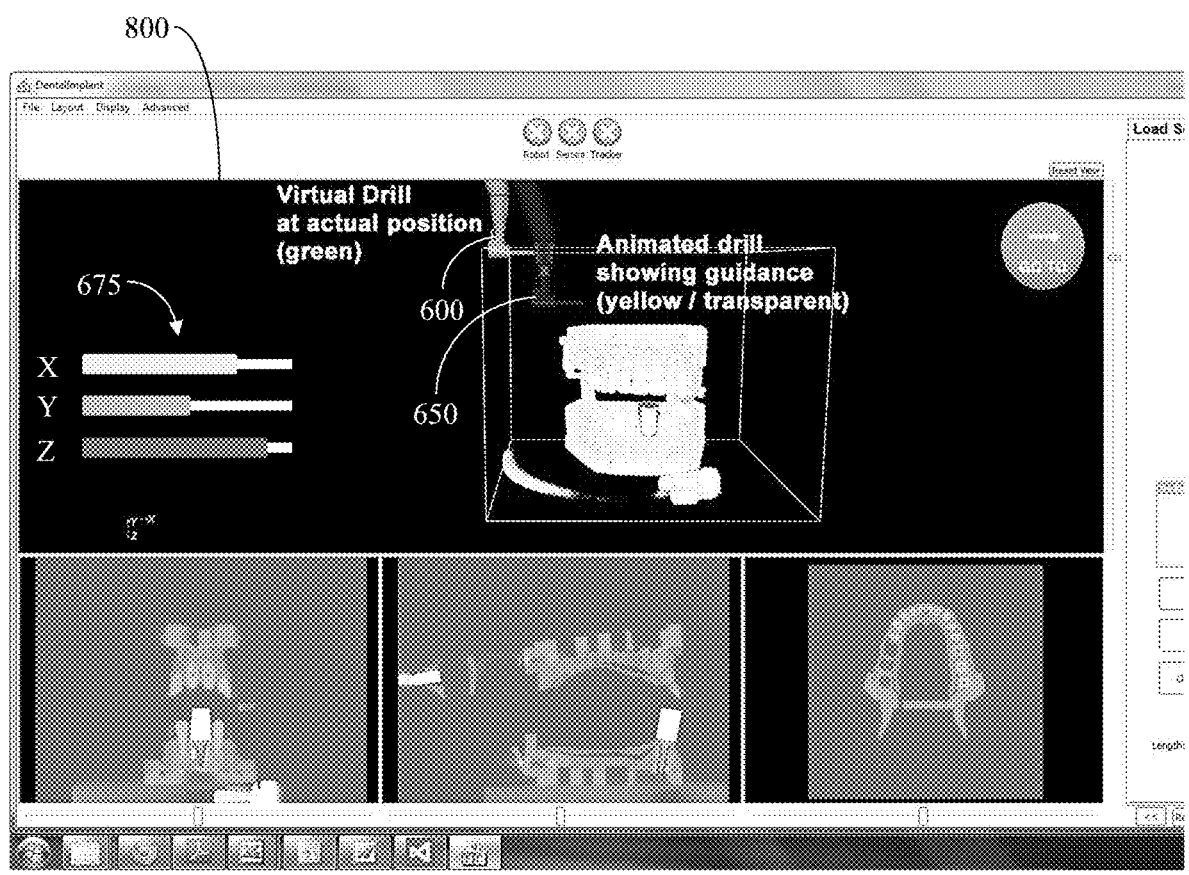
Figure 7:
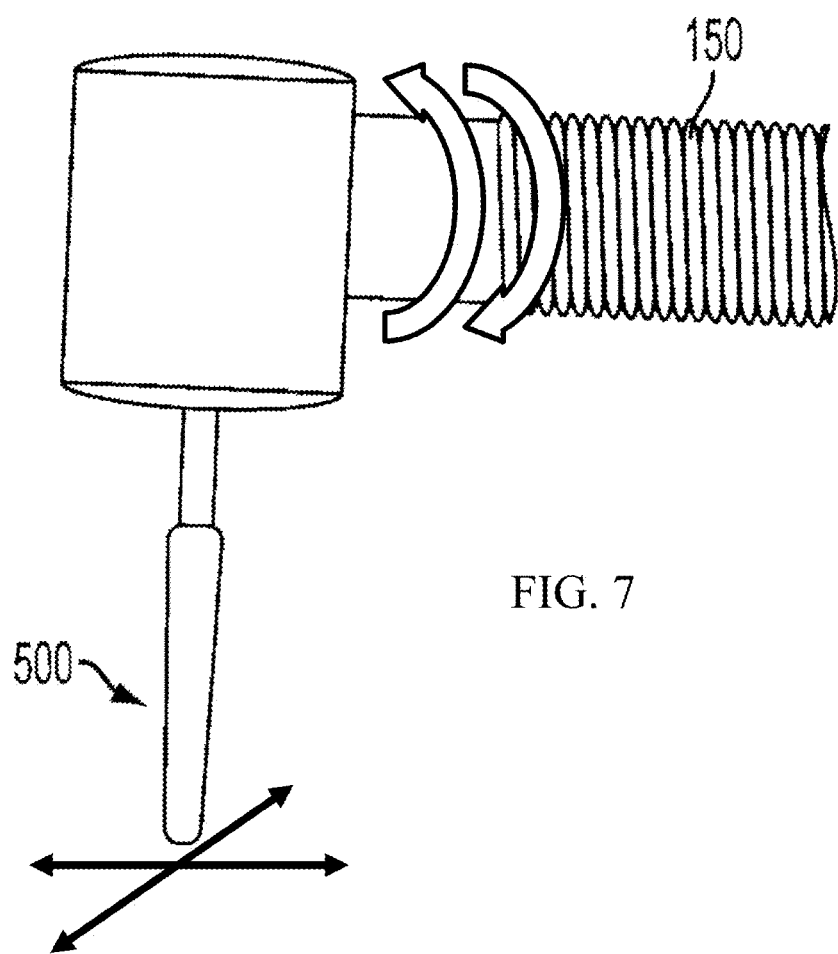

Having thus described the disclosure in general terms, reference will now be made to the accompanying drawings, which are not necessarily drawn to scale, and wherein:

FIG. 1 illustrates a prior art example of a "flight simulator" style of visual guide for a guided medical device;

FIGS. 2A-2C schematically illustrate a dental implantation procedure with respect to the mouth of a patient;

FIGS. 3 and 4 schematically illustrate a dental implantation system, according to various aspects of the present disclosure;

FIG. 5 schematically illustrates a patient-interacting device of a dental implantation system, according to one aspect of the present disclosure;

FIG. 6 schematically illustrates a display of a real-time representation of the patient-interacting device in relation to a representation of the mouth of the patient, and in relation to a virtual representation of the patient-interacting device following a virtual implantation plan, during manipulation of the patient-interacting device, according to one aspect of the present disclosure; and FIG. 7 schematically illustrates manipulation capabilities of a patient-interacting device of a dental implantation system, according to one aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Various aspects of the present disclosure may be at least partially based on a guided surgical robotic system and method such as that disclosed, for example, in U.S. Pat. No. 8,808,000 to Salcedo et al. and assigned to Neocis, also the assignee of the present application. The disclosure of U.S. Pat. No. 8,808,000 to Salcedo et al. is thus incorporated by reference herein.

In this regard, a dental implantation procedure generally involves an invasive incision into the gum of the patient in order to allow the practitioner to view the underlying jawbone structure. A hole is then drilled into the jawbone structure, into which a dental implant is placed (see, e.g., FIG. 2A). In some instances, the dental implant may be shaped, for example, like a screw or other threaded member. Once the dental implant is inserted into the jawbone structure, an external post is attached to the dental implant (see, e.g., FIG. 2B), and a prosthetic cap (i.e., a crown or tooth reproduction) attached to the post (see, e.g., FIG. 2C). With computerized tomography (CT) and other imaging scans becoming more common, the practitioner may be able to graphically visualize the jawbone structure, without or before the invasive incision. However, the alignment of the dental implant with respect to the jawbone structure and/or relative to other implants or teeth may be an important factor in determining, for example, the life of the dental implant, the appearance thereof, and the comfort to the patient. If the dental implant is poorly or otherwise not optimally placed, the dental implant can undesirably fail (or at least have a shorter service life), may undesirably cause other teeth or dental implants to be compromised, and/or damage proximal nerves.

FIGS. 3 and 4 thus illustrate various aspects of a dental implantation system according to the present disclosure, the system being generally indicated by the numeral 100. As previously indicated, current dental implantation procedures generally involve an imaging step, wherein CT or other appropriate images of the patient's jaw structure are obtained, and any anomalies diagnosed (i.e., whether the patient requires bone grafts to prepare the implant area). The practitioner then corrects any anomalies and proceeds with the invasive implant procedure based on the conditions associated with the patient's jaw structure, once the appropriate incisions have been made in the patient's gum. In this regard, one skilled in the art will appreciate that, though the present disclosure provides some exemplary aspects of the various systems and methods implemented with respect to the jaw structure of a patient, the various systems and method disclosed herein may be readily applicable, or otherwise readily adaptable, to other surgical procedures that are proximal to or otherwise capable of being correlated with the fiducial marker associated with the engagement between a splint or other engaging member, and the jaw structure of the patient, as otherwise disclosed herein (i.e., brain surgery, skull surgery, ENT surgery, or any other surgical procedure associated with the head/skull structure of the patient).

A dental implantation system 100 according to various aspects of the present disclosure addresses particular subjective aspects of current dental implantation procedures by providing a guided patient-interacting device 150 (otherwise referred to herein as a "cutting device" or "drilling device" or "site preparation device" or "implantation device" depending on the particular instrument 500 engaged with the patient-interacting device 150 so as to configure the patient-interacting device 150 for a particular corresponding purpose or procedure) configured to be guided with respect to the invasive portion, or at least the patient-interacting portion, of the dental implant procedure (i.e., to "prepare" the site within or otherwise engage the patient's mouth). That is, the patient-interacting device 150 is operably engaged with a guiding device 200, such as, for example, an articulating arm member 350 (i.e., a robotic arm). The guiding device 200 is adapted to operably engage or otherwise be in communication with the mouth of the patient, for example, by way of a splint 250 or other engaging member, forming or otherwise defining a fiducial marker. That is, in one instance, the splint 250 is configured to engage the patient's mouth in a "firm" or secure interaction (i.e., the splint 250 is engaged with the patient's teeth and does not move with respect to the patient's mouth). Since the splint 250 does not move with respect to the patient's mouth, the disposition of the splint 250 is known, and thus can be configured to provide a fiducial marker (i.e., a known origin or coordinate formed by the secure interaction with or otherwise associated with or attached to the splint 250) which can be used, for instance, to guide the patient-interacting device/instrument, via the guiding device 200, to prepare the site in the patient's mouth in association with the dental implant 300 (see, e.g., FIG. 2B).

In one aspect, the splint 250 is configured to be "universally applicable" (i.e., capable of forming the secure engagement with the mouth of any patient), or at least applicable across a particular range of patients (i.e., one size fits a certain size or age of patient). In order to determine a reference associated with the fiducial marker, according to one aspect of the disclosure, the splint 250 may be engaged with the patient's teeth, and the patient's jawbone structure then imaged using, for example, CT or any other suitable imaging technique such as, for instance, MRI. The fiducial marker can thus be established, for instance, as a reference origin of a relative coordinate system.

One skilled in the art will appreciate that the splint 250 may be configured in many different manners to accomplish the desired function as discussed herein. For example, the splint 250 may be rigidly attached to the patient's mouth in an appropriate manner depending on the condition of the patient. That is, if the patient has some strong teeth capable of supporting the splint 250, the splint 250 can be attached to the teeth with an adhesive or with a suitable clamp. For edentulous patients (i.e., without teeth), bone pins may be drilled through the splint 250 and into the patient's jawbone structure to fasten the splint 250 securely into place. The splint 250 may also be attached to the jawbone structure of any patient using, for example, appropriate bone screws. In one aspect, the positioning of the splint 250 with respect to the patient's mouth may not be critical or important, as long as the splint 250 remains rigidly in place. A fiducial marker (not shown) may then be formed by the secure engagement, or may otherwise be attached to, or incorporated into, or associated with the splint 250, wherein the fiducial marker may be configured to have a geometry or other characteristic or feature that uniquely defines the fiducial marker in a three-dimensional space (i.e., such that the fiducial marker is readily identified in images of the patient's jawbone structure, or is otherwise detectable and trackable using a mechanical arrangement, an electrical arrangement, an electromechanical arrangement, an optical arrangement, a magnetic arrangement, or any other suitable detection/tracking arrangement, or combination thereof). In such instances, the fiducial marker may be comprised of, for example, a radiopaque material that can be clearly defined in the image obtained, e.g., by CT or MRI.

In one aspect, the patient-interacting device 150 may be engaged with the guiding device 200, for example, in the form of an articulating arm member or a robotic arm 350, which is configured to determine a range of motion of the patient-interacting device 150/instrument 500 (i.e., translation in a particular direction (horizontal and/or vertical), and/or rotation about an axis). In some instances, the functionality of the guiding device 200 may be included in the configuration and arrangement of the articulating arm member 350, itself. For example, the articulating arm member 350 or portions thereof may include or be engaged with one or more actuators configured and arranged to cooperate to guide a distal end of the articulating arm member 350 in a desired direction and orientation, upon manipulation by the user to accomplish the surgical procedure.

In some instances, the guiding device 200 may further comprise a communication element 400 in communication between the splint 250 and the patient-interacting device 150 and/or between the splint 250 and the arm member 350. For example, the communication element 400 may comprise a mechanical linkage connecting the splint 250 to the patient-interacting device 150 or to the arm member 350. That is, the communication element 400 may comprise, for example, a mechanically- or physically-tracked arm which attaches to the splint 250 engaged with the patient. In some instances, the arm (communication element 400) may be attached to the splint 250 (rigidly and in a known, repeatable manner) with an attachment mechanism comprising a kinematic mount (i.e., a kinematic mount may be engaged between the arm and the splint 250). Attached to the patient in this manner via the attachment mechanism and the splint 250, the communication element 400 may be tracked or otherwise monitored to provide data (whether constantly, selectively, or otherwise as necessary) about the position of the patient (i.e., with respect to the fiduciary or fiducial marker) to the patient-interacting device 150 and/or to the arm member 350, while still providing for accurate guidance of the patient-interacting device 150 and/or the arm member 350, in the event that the patient moves during the surgical procedure.

However, one skilled in the art will appreciate that the splint 250 and/or the fiducial marker determined thereby may be communicated to the patient-interacting device 150 and/or to the arm member 350 in many different manners. For example, instead of or in addition to the physical arm (communication element 400), the fiducial marker may be communicated via a communication element 400 comprising a wireless transceiver, a hardwire connection, an optical communication system (i.e., a camera or other video device), an acoustic tracking system, or any other suitable mechanism, whether electrical, mechanical, electromechanical, acoustic, or optical in nature. That is, in various instances, the kinematic mount, itself, may comprise an attachment point for a tracking portion (and/or the tracking arm or other tracking provision) associated with the guidance system for the surgical robot (i.e., wherein, for instance, reflective markers may be mounted to the attachment point for optical tracking of the fiducial marker or the splint device itself, or the attachment point may include a securing site for forming a mechanical connection therewith for mechanical tracking of the fiducial marker, or the attachment point may otherwise be configured to receive an appropriate element associated with any other suitable tracking arrangement for the fiducial marker, whether electrical, mechanical, electromechanical, acoustic, or optical in nature). In other aspects, the kinematic mount may be configured or otherwise arranged to function as a fixed mounting site for particular tracking devices such as, for example, one or more markers that may be permanently affixed to the kinematic mount 500 and configured to be trackable by an optical-type tracking device (i.e., an optical tracking marker).

In any instance, the system 100 may be further configured to include a controller device 450 (i.e., a computer device as shown in FIG. 4) for determining, controlling, or tracking the fiducial marker with respect to the image of the patient's mouth having the splint 250 disposed therein. The controller device 450 may also be configured and arranged to appropriately communicate the fiducial marker to the patient-interacting device 150 and/or to the arm member 350. In some aspects, the system 100 or the controller device 450 may also comprise a planning device or otherwise include planning functionality for allowing a user to develop the virtual implantation plan, as otherwise disclosed herein, in conjunction with the hardware and/or software of the system 100.

In one aspect, the controller device 450 may be further configured to receive the image of the patient's jawbone structure (having the splint 250 therein). In some instances, the controller device 450, which includes a processor, may be further configured to be capable of executing a planning routine that may comprise software, hardware, or a combination thereof (i.e., a planning device and/or planning functionality). The planning routine thus allows the practitioner to create, for example, a virtual implantation plan based on the captured image(s), whether in two dimensions or three dimensions, and to manipulate the image(s) of the patient's jawbone structure in conjunction with a "virtual implant" in order to develop the virtual implantation plan or placement determination of the prosthesis for the patient, in conjunction with a computerized model based on the image(s). In some aspects, the planning routine, virtual implantation plan, and/or placement determination may be created in relation, for example, to a coordinate system (relative or absolute), as will be appreciated by one skilled in the art, configured to associate the planning parameters with the fiducial marker. In other aspects, the controller device 450 and/or the planning device associated therewith may include a peripheral device (i.e., a trackball or joystick in conjunction with, for example, 3D goggles, all not shown) to assist with or otherwise permit virtual manipulation of the placement of the virtual implant(s) with respect to the image(s) of the patient's jaw structure in order to, for example, align the implant(s) relative to each other or relative to adjacent teeth, to align the implant(s) relative to the affected nerve, and/or to align the implant(s) relative to the jawbone structure. The controller device 450 and/or the planning device may be further configured to perform such manipulation manually, automatically, or semi-automatically, as necessary or desired. Because the virtual implant(s) may be manipulated in a similar manner to the image(s), the orientation or placement of the virtual implant(s) may represent the desired actual placement of the implant with respect to the patient's jawbone structure, thus providing an intuitive interface for planning the implantation procedure.

In aspects where the splint 250/fiducial marker approach is used, the patient is automatically registered with the system 100/controller device 450 once the communication element 400 is attached to or otherwise engaged or in communication with the splint 250 via the kinematic mount of the attachment mechanism. That is, the fiducial marker is automatically determined from the image(s) of the patient's jawbone structure, and the alignment and location thereof in physical space is known due to the kinematic mount connecting the communication element 400 (i.e., arm) to the splint 250. One skilled in the art will appreciate, however, that other alignment approaches may be implemented that do not necessarily require a fiducial marker. For example, in some instances, a surface matching technique can be implemented. More particularly, the patient's jawbone structure may be manipulated into a 3D configuration in the captured image(s). A suitable scanning device (i.e., a physical pointer or other imaging device such as an ultrasound transducer or OCT (optical coherence tomography) scanner may be attached to an end effector (i.e., tip) of the arm member 350 such that the tip of the arm member 350 is capable of scanning the patient's jawbone structure to "surface match" the captured and manipulated image(s) with an actual scan of the jawbone structure, as administered, for example, via the controller device 450.

One skilled in the art will further appreciate that the association of the fiducial marker with the patient's anatomy, via the controller device 450, may be accomplished in different manners. For example, with respect to the registration of the image (e.g., CT scan) to the fiducial marker, one method could involve the jaw structure of the patient being imaged with the fiducial marker in place, as previously discussed, wherein the patient would then be substantially immediately subjected to the implantation procedure. Such a scheme may be beneficial, for example, in reducing the number of visits to the practitioner by the patient. However, in some instances, the practitioner may not have the imaging capabilities at hand, or may prefer to carefully determine the virtual implantation plan before carrying out the implantation procedure. In both such instances, the patient will likely be required to return to the practitioner at a later time. Accordingly, in such situations, a pre-operative imaging procedure (e.g., CT scan) may be performed on the jaw structure of the patient, without a fiducial marker in place (i.e., a "normal" scan by which the practitioner can determine the virtual implantation plan). This pre-operative imaging procedure can thus be performed, for example, at the practitioner's site, or at a dedicated scanning/imaging center. Subsequently, immediately prior to the implantation procedure being performed, and with the fiducial marker(s) engaged with the jaw structure of the patient, the practitioner may capture another image (e.g., CT scan, panoramic x-ray, or two single x-rays) of the patient's jaw structure. The controller device 450/planning device may thus also be configured to correlate the pre-operative image (used to determine the virtual implantation procedure) with the "day of" image so as to register the fiducial marker(s) with respect to the original pre-operative image. Such a registration or correlation procedure may be implemented in hardware, software, or a combination thereof, as will be appreciated by one skilled in the art. The implantation procedure could then proceed as otherwise disclosed herein.

In any instance, the communication element 400 may be configured to communicate with the arm member 350 in a manner known to the system 100, such that the position/movement characteristics of the end effector/tip thereof are also known. This engagement between the communication element 400 and the arm member 350 thus allows the patient-interacting device 150/instrument 500 (i.e., the end effector/tip) to be registered with respect to the fiducial marker (or other reference with respect to the patient) attached to the patient via the splint 250, the kinematic mount, the communication element 400, and the arm member 350. In this manner, the virtual implantation process, planned through the controller device 450/planning device, may be accomplished in relation to the fiducial marker (or other reference with respect to the patient) and thus translated or otherwise communicated to the system 100 for directing the patient-interacting device 150/instrument 500 via the guiding device 200 and the arm member 350. As previously disclosed, and as will be appreciated by one skilled in the art, the communication element 400 may, in some instances, be configured to communicate between the splint 250/kinematic mount and the controller device 450/planning device (and/or between the splint 250/kinematic mount and the patient-interacting device 150/instrument 500), based upon the premise of establishing a known association of the fiducial marker with the patient's anatomy, in relation to which the guiding device 200 is used to guide the patient-interacting device 150/instrument 500 via the arm member 350 during the implantation procedure.

The patient-interacting device 150/instrument 500 may comprise, be disposed in, or otherwise engaged with the end effector of the arm member 350 (robotic arm). The arm member 350 may be configured, for example, to provide six degrees of freedom and can also be configured to restrict or otherwise control the movement of the patient-interacting device 150/instrument 500. Further, in some instances, the arm member 350 may have a miniature parallel structure to which the patient-interacting device 150 is secured and allowed to have full freedom of movement when not in cutting/preparation/implantation mode. Since the patient-interacting device 150/instrument 500 comprises or is attached to the end effector of the arm member 350, the patient interacting portion (i.e., the cutting/drilling tip) is the instrument 500 (see, e.g., FIG. 3) of the patient-interacting device 150, and the instrument 500 thus must be in a known position (i.e., known to the system 100/controller device 450) relative to the arm member 350. In some aspects, in order to calibrate the interacting portion/instrument 500 of the patient-interacting device 150 with respect to the fiducial marker, a calibration element may be engaged with the patient-interacting device 150 via a kinematic coupling (i.e., rigidly mounted thereto in a known, repeatable manner). One skilled in the art will thus appreciate that the interacting portion/instrument 500 of the patient-interacting device 150 can then be calibrated with various tip calibrating methods (i.e., invariant point, etc.). Once calibrated, the calibration element is replaced with a cutting/drilling element (instrument 500) in the patient-interacting device 150, in a known and repeatable manner, so that the calibration parameters (i.e., the position of the distal-most point and axis of cutting/drilling) associated with the interacting portion/instrument 500 are maintained as calibrated.

With the alignment with respect to the patient established and known by the system 100/controller device 450, and the virtual implantation plan developed through the controller device 450/planning device, the implantation procedure (i.e., cutting/drilling/insertion) can then be initiated by the practitioner moving the patient-interacting device 150/instrument 500 toward the patient's mouth (having the splint 250 engaged therewith). In such instances, the controller device 450/planning device is configured to control, restrict, or otherwise modulate the movement of (or the practitioner's ability to move) the patient-interacting device 150 via the arm member 350 such that the action of the practitioner merely moves the interacting portion/instrument 500 (i.e., the cutting/drilling element) to the appropriate starting position for the implantation procedure, with respect to the patient's jawbone structure, as determined by the controller device 450/planning device and dictated by the virtual implantation plan. Once the cutting/drilling element is in the position dictated by the controller device 450/planning device, the invasive portion of the procedure can then be initiated, wherein the controller device 450/planning device may further dictate other parameters of the implantation device 150/instrument 500 such as, for example, the orientation of the path of the cutting/drilling element (instrument 500) and the cutting/drilling distance along that path from the cutting/drilling origin, also according to the virtual implantation plan. In some instances, the system 100 disclosed herein may be configured such that the patient-interacting device 150 is not guided by the practitioner, but is only urged by the practitioner along a procedural route determined via the virtual implantation plan and implemented via the controller device 450/planning device and the arm member 350. That is, the system 100 may be configured to restrict the practitioner to performing the implantation procedure with respect to the patient, as determined via the virtual implantation plan and implemented via the controller device 450/planning device and the arm member 350, whereby the controller device 450/planning device controls the allowable movement of the arm member 350 (and thus the patient-interacting device 150/instrument 500) in accordance with the virtual implantation plan created from the image(s) of the patient's jawbone structure. For instance, the system 100 may be configured for restricted movement of the arm member 350/patient-interacting device 150/instrument 500, as communicated to the practitioner through tactile/haptic feedback, where, for example, the arm member 350/patient-interacting device 150/instrument 500 may be easier to move according to the virtual implantation plan, and more difficult to move if deviating from the virtual implantation plan.

One skilled in the art will also appreciate, however, that the physical structure of the arm member 350/patient-interacting device 150/instrument 500 may not necessarily be configured to provide full and absolute controlled movement according to the virtual implantation plan (i.e., due to vibration, flexing of components, gravity, and/or excessive force applied by the practitioner) and, as such, the system 100/controller device 450 may be further configured to provide other manners of feedback to the practitioner such as, for example, via a deviation warning indicia, haptic feedback, or any other suitable audio and/or visual and/or any other suitable mechanism. Therefore, the system 100/controller device 450 includes provisions for actually implementing the virtual implantation plan, and thus facilitates a more accurate implantation procedure, rather than merely warning the practitioner if any procedural parameters may be inaccurate. One skilled in the art will also appreciate, however, that, in some instances, the system 100 may be further configured to autonomously accomplish the virtual implantation plan, without the manipulation of the practitioner, through automatic manipulation of the arm member 350/patient-interacting device 150/instrument 500 via the controller device 450/planning device.

In one exemplary surgical procedure using a dental implantation system 100, as disclosed herein, the splint 250 (i.e., mouthpiece) is first attached to the patient's teeth, and thus provides or is associated with a fiducial marker. The patient's jawbone structure is then imaged (with the splint 250 in place and engaged with the patient's teeth) using, for example, CT or any other appropriate imaging technique (e.g., MRI), and the image(s) communicated to the controller device 450. The controller device 450 may be further configured to be capable of executing an implantation routine, thus allowing the practitioner to develop an implantation plan for the patient, for example, by manipulating a virtual implant with respect to the captured image(s). Once the virtual implantation plan is created, the communication element 400 is engaged with (i.e., attached to the patient's mouth, with the patient being positioned in a suitable position to initiate the procedure) or otherwise placed into communication with the splint 250 (i.e., via the kinematic mount). The arm member 350, patient-interacting device 150, and interacting portion/instrument 500 thereof, are then calibrated by the practitioner (or automatically by the controller device 450), before the actual cutting/drilling element (instrument 500) of the patient-interacting device 150 is used by the practitioner (or autonomously via the controller device 450/planning device), via the patient-interacting device 150 as guided by the arm member 350 and the controller device 450, to accomplish the implantation procedure as planned and dictated by the virtual implantation plan.

In some instances, as previously discussed, haptic or feedback-based robotic systems may be configured to interact with the user/surgeon by responding to the forces applied by the user/surgeon during the procedure. For example, the surgical instrument (i.e., drill) may be generally arranged to be mounted on or in association with suitable force sensors. In instances of haptic robotic systems implementing an arrangement of one or more robotic arms to which the surgical instrument is mounted, "gravity compensation" may sometimes be required to counteract or compensate for the force of gravity on the arm(s) (i.e., in order to make the arm(s)/surgical instrument feel weightless to the user/surgeon). However, since there is an element of interactivity with the user, such a system may sometimes have difficulty discerning between the various forces involved and acting upon the arm(s)/surgical instrument such as, for example force applied by the user, any drift of the force sensor which may result in the detection of "phantom" forces, the force of gravity, or the force of resistance (i.e., from the drill drilling into the patient's bone structure). As a result, the counteracting or compensating force may not accurately correlate to the actual forces involved and acting upon the arm(s)/surgical instrument at a given time.

As such, aspects of the present disclosure (see, e.g., FIGS. 3 and 4) may provide a dental implantation system 100, as previously disclosed, wherein the patient-interacting device 150/instrument 500 is adapted to at least interact with and prepare a site within a mouth of a patient for receiving a dental implant, and the guiding device 200 in communication with the fiducial marker is configured to receive the patient-interacting device 150, and to guide the instrument 500 relative to the fiducial marker, in conjunction with manipulation of the patient-interacting device 150 by the user. The controller device 450, including a processor, is configured to be in communication with the guiding device 200, and to direct the patient-interacting device 150 via the guiding device 200 to prepare the site to receive the dental implant. In such particular aspects, an engagement sensor 750 is operably engaged with the patient-interacting device 150 (see, e.g., FIG. 5), wherein the engagement sensor 750 is configured to be in communication with the controller device 450. The engagement sensor 750 is further configured to be responsive to disengagement between the patient-interacting device 150 and the user, so as to direct the guiding device 200 to at least maintain the patient-interacting device 150 at a minimum vertical disposition.

That is, as previously noted, because of interactivity with the user, the system may sometimes have difficulty discerning between the various forces involved and acting upon the arm member 350/patient-interacting device 150 such as, for example force applied by the user, any drift of the force sensor which may result in the detection of "phantom" forces, the force of gravity, or the force of resistance (i.e., from the drill drilling into the patient's bone structure), etc. As a result, the counteracting or compensating force provided by the controller 450 (i.e., by way of the arm member 350) may not accurately correlate to the actual forces involved and acting upon the arm(s)/surgical instrument at a given time. As such, the engagement sensor 750 is arranged with respect to the patient-interacting device 150 so as to determine when the user is actively engaged or disengaged from the patient-interacting device 150 (i.e., whether the user is gripping the patient-interacting device 150 or not). By being able to determine when the user is not actively engaged with the patient-interacting device 150, the controller device 450 may be able to eliminate any effects of drift on the patient-interacting device 150 by the guiding device 200 (i.e., since the engagement sensor 750 is not actuated, the controller device 450 knows that any indicated forces on the guiding device 200/patient-interacting device 150 are not originating from use interaction with the patient-interacting device 150). More particularly, for example, as a safety measure, the determination of disengagement between the patient-interacting device 150 and the user by the engagement sensor 750 may cause the controller device 450 to direct the guiding device 200 to at least maintain the patient-interacting device 150 at a minimum vertical disposition (i.e., the patient-interacting device 150/arm member 350 is prevented from falling or downwardly creeping due to gravity), upon release of the patient-interacting device 150 by the user. Thereafter, any movement of the guiding device 200, arm member 350, and/or the surgical instrument (i.e., the patient-interacting device 150/instrument 500), in instances where the user is not actively engaged with or holding the surgical instrument, may be readily detected by the controller device 450 and the disengaged position of the patient-interacting device 150 to be determined. Further, in some instances, at least one force sensor may be operably engaged with, for example, the guiding device 200 and/or the patient-interacting device 150, wherein the at least one force sensor may be configured to measure a force or forces acting on the patient-interacting device 150, and to communicate the measured force to the controller device 450. In such instances, the controller device 450 may be responsive to the determination of disengagement from the engagement sensor 750 by the user to zero the measured force from the at least one force sensor (i.e., such that any indicated forces later appearing on the guiding device 200/patient-interacting device 150 are ascertained to not be originating from use interaction with the patient-interacting device 150).

In other instances, the engagement sensor 750 may be further configured to be responsive to disengagement between the patient-interacting device 150 and the user to direct the guiding device 200 (i.e., via the controller device 450) to maintain the patient-interacting device 150 at a selected lateral disposition and/or a selected rotational orientation. That is, in addition to or in the alternative to maintaining the patient interacting device 150 at a minimum vertical disposition, the patient-interacting device 150 may also be restricted from moving laterally or sideways, or rotating about the longitudinal axis thereof, by the controller 450/guiding device 200, if the engagement sensor 750 does not detect engagement between the user and the patient-interacting device 150. Further, in other instances, the engagement sensor 750 may be configured to be responsive to engagement between the patient-interacting device 150 and the user to actuate the guiding device 200, for example, by way of the controller device 450, to guide at least the instrument 500 of the patient-interacting device 150, relative to the fiducial marker, and/or to direct the controller device 450 to actuate the virtual implantation plan for guiding at least the instrument 500 of the patient-interacting device 150. Additionally, the engagement sensor 750 may be configured to be responsive to engagement between the patient-interacting device 150 and the user to at least permit the instrument 500 to be actuated. That is, in particular instances, the engagement sensor 750 may require the detection of engagement between the patient-interacting device 150 and the user in order for the patient-interacting device 150/instrument 500 to be actuatable or otherwise operable to carry out the surgical procedure. Moreover, the user may be required to engage the patient-interacting device 150, as detected by the engagement sensor 750, in order to allow the virtual implantation plan to be actuated and/or for the guiding device 200 to provide the appropriate guidance for the user-manipulated patient-interacting device 150. That is, in some aspects, the system 100 may be configured such that the controller device 450 is configured to execute the virtual implantation plan for the site within the mouth of the patient, and to direct the guiding device 200 according to the virtual implantation plan, in response to engagement of the engagement sensor 750 by the user. In some of these aspects, the controller device 450 may be configured to direct tactile feedback to the user, via the patient-interacting device 150 (i.e., tactile or haptic feedback via the patient-interacting device to the hand of the user grasping the patient-interacting device 150 and engaging the engagement sensor 750), if the instrument 500 manipulated by the user deviates from the virtual implantation plan. Further, the controller device 450 may be configured to direct at least one of audio feedback and visual feedback to the user, via at least one of the controller device 450 and the patient-interacting device 150, if the instrument 500 manipulated by the user deviates from the virtual implantation plan.

In another aspect, the system 100 may further comprise a display device 800 (see, e.g., FIGS. 4 and 5) in communication with the controller device 450 and/or the patient-interacting device 150. The display device 800 may be configured to display a real-time representation of at least the instrument 500 of the patient-interacting device 150, in relation to a representation of the mouth of the patient, during engagement with and manipulation of the patient-interacting device 150 by the user. In such instances, the controller device 450 may also be configured to be in communication with the guidance device 200 and the display device 150, wherein the controller device 450 may be configured to monitor manipulation of at least the instrument 500 of the patient-interacting device 150 by the user, in relation to the mouth of the patient, at least partially via the guidance device 200, and to direct information associated therewith to the display device 800.

The engagement sensor 750 may be implemented in many different manners, as will be appreciated by one skilled in the art. In some instances, the engagement sensor 750 may be operably engaged with the patient-interacting device 150, and may comprise, for example, one of a touch-sensitive actuator, a pressure-sensitive actuator, an optical actuator, and an acoustic actuator, associated with the patient-interacting device 150. For example, detection of the user's grip on the patient-interacting device 150 may be implemented by way of, for example, an engagement sensor 750 comprising a camera, an infrared sensor, an acoustic sensor, a range-finder, or other appropriate sensor that is engaged with or in proximity to the patient-interacting device 150 to determine if actual contact is made with the patient-interacting device 150, or if an object that can be identified, for example, as a hand of the user, intercedes between the sensor and the patient-interacting device 150. In other instances, for example, the engagement sensor 750 may comprise, for example, an appropriate pressure switch or sensor mounted on the patient-interacting device 150, a sleeve placed over the patient-interacting device 150 which, in cooperation, can indicate physical contact by closing an electrical contact or sensing pressure in response to the grip of the user's hand. In some instances, the engagement sensor 750 may also be configured to measure or otherwise determine the magnitude of the force exerted via the user's grip on the patient-interacting device 150, wherein the measured force magnitude could be directed to the controller device 450 or elsewhere in the system 100 as necessary or appropriate.

The engagement sensor 750 (as well as other components such as, for example, the fiducial marker), may be established in communication with the controller device 450 and/or other components in the system 100, for example, by way of an electrical communication system, a mechanical communication system, an electromechanical communication system, an optical communication system, and combinations thereof, or through any other suitable communication arrangement, as will be appreciated by one skilled in the art, wherein the communication system or communication arrangement may, for example, comprise a wireless communication system and/or a wired communication system.

In another aspect, the planning of or actually conducting the surgical procedure by way of, for instance, the controller device 450 and/or the planning device and/or planning functionality associated therewith, may be enhanced by incorporating real-time intuitive feedback into the virtual implantation plan (i.e., as opposed to the virtual implantation plan being created solely based upon the imaging of the patient's mouth and used as a reference by the surgeon). For example, in such aspects, a drill, probe, or other instrument 500 engaged with or forming the patient-interacting device 150, whether engaged with the system 100 as disclosed herein or arranged separately in communication with the system 100 (i.e., tracked by camera or other optical device, attached to a mechanical arm having a known or trackable range of motion, tracked by an acoustic tracking, or otherwise maintained in communication with a reference point) may be manipulated by the user (i.e., surgeon) in relation to the site within the patient's mouth. In doing so, the manipulation of the patient-interacting device 150/instrument 500 by the user can be monitored in real-time by the controller device 450/planning device, in relation to the actual anatomy associated with the site within the patient's mouth or in relation to a model thereof. In such instances, the system 100 may also include a display device 800 (see, e.g., FIGS. 4 and 5) in communication with the controller device 450/planning device, and configured to receive and display a real-time representation of the patient-interacting device 150/instrument 500 in relation to a representation of the mouth of the patient (i.e., the actual anatomy imaged during the manipulation or a model or other representation thereof otherwise determined) during manipulation of the patient-interacting device 150, such that the user can see or visualize feedback of the manipulation of the patient-interacting device 150/instrument 500 on the display device 800 in real time. That is, the dental implant position, the site within the patient's mouth, and/or the surgical (dental implantation) plan could be projected in a virtual manner on the display device 800, such that the user could visualize a simulation of the surgical procedure in relation to the physical manipulation of the patient-interacting device 150/instrument 500 by the user, and in real time. For example, an implantation device 150 having a prosthetic member attached thereto may be moved or manipulated in relation to the site in the patient's mouth, and the user may concurrently view a representation of the implantation device 150 having the virtual dental implant engaged therewith on the display device 800, in relation to a virtual projection of the interaction of the dental implant with the site within the patient's mouth, while the manipulation is occurring.

In some instances, the controller device 450/planning device may be configured to relate the manipulation of the patient-interacting device 150/instrument 500 by the user to a previously-developed virtual implantation plan (or even initiate a virtual implantation plan based upon the manipulation), such that the virtual implantation plan can be updated and/or modified in relation to the manipulation by the user. Further, when a satisfactory "virtual" position of the dental implant is achieved, or at any point selected by the user, the virtual implantation plan can finalized or "locked in" by the user (i.e., the user can selectively indicate that the updates/modifications to the virtual implantation plan resulting from the manipulation are satisfactory, and the previously-existing virtual implantation plan can thus be updated/amended to include the same). In some particular aspects, the finalized virtual implantation plan may be executed by the controller device 450/planning device, with the system 100 being configured to be responsive to the executed virtual implantation plan to direct the manually-guided patient-interacting device (i.e., using haptic or tactile feedback to the user) or to direct an autonomous robotic system.

In order to facilitate intuitive guidance or reference for the user in relation to the virtual implantation plan (i.e., provide intuitive guidance to the user for carrying out the virtual implantation plan using the patient-interacting device 150), aspects of the present disclosure may also provide a dental implantation system 100, as previously disclosed, wherein the display device 800 (see, e.g., FIG. 6) is configured to display a real-time representation of the instrument 500 of the patient-interacting device 150 (see, e.g., FIG. 7), in relation to a representation of the mouth of the patient, during manipulation of the patient-interacting device 150 by the user. In addition to displaying the real-time representation of the instrument 500 of the patient-interacting device 150, in relation to a representation of the mouth of the patient, on the display device 800, the controller device 450 may further be configured to 1) direct the display device 800 to display the real-time representation 600 of the instrument 500 in relation to a virtual representation 650 of the instrument 500 of the patient-interacting device 150 manipulated in accordance with the virtual implantation plan; 2) direct an audio device 700 (see, e.g., FIG. 5) in communication with the controller device 450 to emit a selected audio signal indicative of the patient-interacting device 150 manipulated in accordance with the virtual implantation plan; and/or 3) direct the guiding device 200 to provide a selected resistance to manipulation of the patient-interacting device 150 in accordance with the virtual implantation plan.

For example, the controller device 450 may be further configured to direct the display device 800 to display an animation of the virtual representation 650 of the instrument 500 of the patient-interacting device 150 manipulated in accordance with the virtual implantation plan, wherein the animation may originate from a current disposition of the real-time representation 600 of the instrument 500 of the patient-interacting device 150 also displayed by the display device 800. That is, the animation of the virtual representation 650 of the instrument 500 may indicate, via the animation, the direction (i.e., horizontal and/or vertical) in which the user must direct the patient-interacting device 150 and/or the direction of rotation in which the user must rotate the patient-interacting device 150 (see, e.g., FIG. 7), starting from the current disposition of the real-time representation 600 of the instrument 500, in order to move or manipulate the instrument 500 according to the virtual implantation plan.

In some instances, the controller device 450 may be further configured to direct the display device 800 to display a progress indicia 675, originating from the disposition of the real-time representation of the instrument 500 of the patient-interacting device 150, and progressing in relation to a required manipulation of the patient-interacting device 150 for the instrument 500 to be in accordance with the virtual implantation plan. That is, for example, in addition to the animation, the display device 800 may also display some indication of the progress of the user in moving the patient-interacting device 150 toward the site of the procedure. Such an indication could be a progress bar graph indicating the distance or rotation that must occur from the current real-time representation of the instrument 500 to the surgical site, or the distance or rotation that must still occur before the instrument 500 is properly manipulated at the surgical site according to the virtual implantation plan. That is, the progress indicia 675 may comprise one of a distance originating from the disposition of the real-time representation of the instrument to a disposition of the instrument in accordance with the virtual implantation plan, and a degree of rotation originating from the disposition of the real-time representation of the instrument to a disposition of the instrument in accordance with the virtual implantation plan.

In instances where an audio device is provided for feedback purposes, the audio device 700 may be configured, for example, to emit a selected audio signal, wherein the selected audio signal may increase or otherwise change in frequency from the disposition of the real-time representation of the instrument toward a disposition of the instrument in accordance with the virtual implantation plan.

In still other aspects, the guiding device 200 may be configured to provide a low resistance to manipulation of the patient-interacting device 150, for instance, when the patient-interacting device 150 is manipulated by the user to move the instrument 500 along a pathway in accordance with the virtual implantation plan, and/or the patient-interacting device 150 is manipulated by the user to rotate the instrument 500 to a degree of rotation in accordance with the virtual implantation plan. Moreover, the guiding device 200 may be further configured to provide a high resistance to manipulation of the patient-interacting device 150 by the user, for example, if the movement of the instrument 500 along the pathway and/or the rotation of the instrument 500 deviates from the virtual implantation plan. That is, the guiding device 200 may be configured such that relatively less force is required from the user to move the patient-interacting device 150 according to the virtual implantation plan, while there may be significant resistance from the guiding device 200 if the user attempts to move the patient-interacting device 150 in deviation from the virtual implantation plan.

Accordingly, in some aspects, various combinations of feedback measures may be implemented by the system 100 that may help to make the user's manipulation of the patient-interacting device 150 according to the virtual implantation plan more intuitive. For example, visual feedback using a "ghost" tool (i.e., a "ghost" instrument of a distinct color may be animated on the display device toward the destination of the surgical site, from the current instrument position. The "ghost" tool may, in some instances, be provided in three-dimensions, with the 3D view may serve to clarify and make more intuitive to the user the direction in which the actual tool must be manipulated according to the virtual implantation plan. In addition, a progress bar indicating "distance to goal" (in degrees for rotation or in a linear measurement for translation), may be provided. The animation and the progress bar may be updated dynamically as the patient-interacting device 150 is manipulated by the user. Further, audio feedback may be used, for example, in the form of a dynamic beeping frequency, to indicate how close the patient-interacting device 150 is to the planned surgical site. In such instances, for example, a lower frequency (i.e., slower) beeping may be audible when the patient-interacting device 150 is relatively far from the intended surgical site, while the frequency of the beeping may increase (i.e., faster) as the patient-interacting device 150 approaches the surgical site.

In some aspects, physical (haptic or tactile) feedback may be implemented, for example, to limit or restrict the motion of the guiding device 200 (i.e., arm member 350) so the user is strictly allowed to guide the patient-interacting device 150 along a particular path (in translation and/or rotation). In some instances, directional damping may also be provided via the guding device 200/arm member 350, for example, to provide cues to the user that the patient-interacting device 150 is being moved the correct manner according to the virtual implantation plan. For example, using directional damping, the guiding device 200/arm member 350 may be configured to provide relatively less resistance to movement of the patient-interacting device 150 along a "proper direction" according to the virtual implantation plan, and/or may be configured to provide relatively more or otherwise significant resistance to movement of the patient-interacting device 150 in the "wrong direction" deviating from the virtual implantation plan. This relatively more resistance is not necessarily absolute resistance, but may allow, for example, the user to move the patient-interacting device 150 backwards in relation to the virtual implantation plan. Such an aspect may be useful, for example, for translation of the patient-interacting device 150/instrument 500 in small spaces and/or rotation of the patient-interacting device 150/instrument 500 where the goal orientation is not necessarily easy to discern.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A dental implantation system, comprising:
    a patient-interacting device having an instrument adapted to at least interact with and prepare a site within a mouth of a patient for receiving a dental implant;
    a guiding device comprising an articulating arm member in communication with a fiducial marker adapted to be engaged with the mouth of the patient, the articulating arm member being configured to receive the patient-interacting device at a distal end thereof, and to guide the instrument of the patient-interacting device, relative to the fiducial marker, in conjunction with manipulation of the patient-interacting device by a user;
    a controller device including a processor, the controller device being configured to be in communication with the articulating arm member, and to direct the patient-interacting device via the articulating arm member to prepare the site to receive the dental implant; and
    an engagement sensor operably engaged with the patient-interacting device, and configured to be in communication with the controller device, the engagement sensor being configured to sense disengagement between the patient-interacting device and the user and to communicate the disengagement to the controller device, the controller device being responsive to the sensed disengagement to direct the articulating arm member to at least maintain the patient-interacting device at a minimum vertical disposition.

2. The system according to claim 1, wherein the controller device is further configured to be responsive to the sensed disengagement between the patient-interacting device and the user to direct the articulating arm member to maintain the patient-interacting device at one of a lateral disposition and a rotational orientation.

3. The system according to claim 1, wherein the controller device is further configured to be responsive to engagement between the patient-interacting device and the user to actuate the articulating arm member to guide at least the instrument of the patient-interacting device, relative to the fiducial marker.

4. The system according to claim 1, wherein the controller device is further configured to be responsive to engagement between the patient-interacting device and the user to at least permit the instrument to be actuated.

5. The system according to claim 1, wherein the controller device is further configured to be responsive to engagement between the patient-interacting device and the user to actuate a virtual implantation plan for guiding at least the instrument of the patient-interacting device.

6. The system according to claim 1, wherein the engagement sensor comprises one of a touch-sensitive actuator, a pressure-sensitive actuator, an optical actuator, and an acoustic actuator, associated with the patient-interacting device.

7. The system according to claim 1, wherein the engagement sensor is configured to be in communication with the controller device via one of an electrical communication system, a mechanical communication system, an electromechanical communication system, an optical communication system, and combinations thereof.

8. The system according to claim 1, wherein the engagement sensor is configured to be in communication with the controller device via one of wireless communication system and a wired communication system.

9. The system according to claim 1, further comprising at least one force sensor operably engaged with at least one of the articulating arm member and the patient-interacting device, the at least one force sensor being configured to measure a force acting on the patient-interacting device, and to communicate the measured force to the controller device.

10. The system according to claim 9, wherein the controller device is responsive to disengagement from the engagement sensor by the user to zero the measured force from the at least one force sensor.

11. The system according to claim 1, wherein the controller device is configured to execute a virtual implantation plan for the site within the mouth of the patient, and to direct the articulating arm member according to the virtual implantation plan, in response to engagement of the engagement sensor by the user.

12. The system according to claim 11, wherein the controller device is configured to direct tactile feedback to the user, via the patient-interacting device, if the instrument manipulated by the user deviates from the virtual implantation plan.

13. The system according to claim 11, wherein the controller device is configured to direct at least one of audio feedback and visual feedback to the user, via at least one of the controller device and the patient-interacting device, if the instrument manipulated by the user deviates from the virtual implantation plan.

14. The system according to claim 1, further comprising a display device configured to display a real-time representation of at least the instrument of the patient-interacting device, in relation to a representation of the mouth of the patient, during engagement with and manipulation of the patient-interacting device by the user.

15. The system according to claim 14, wherein the controller device is configured to be in communication with the articulating arm member and the display device, and wherein the controller device is configured to monitor manipulation of at least the instrument of the patient-interacting device in relation to the mouth of the patient, at least partially via the articulating arm member, and to direct information associated therewith to the display device.

16. A dental implantation method, comprising:
guiding an instrument of a patient-interacting device, via a guiding device comprising an articulating arm member and relative to a fiducial marker adapted to be engaged with a mouth of a patient, in conjunction with manipulation of the patient-interacting device by a user, the patient-interacting device being received by a distal end of the articulating arm member, and the instrument being configured to interact with and prepare the site within the mouth of the patient for receiving a dental implant;
directing the patient-interacting device, via the articulating arm member, to prepare the site to receive the dental implant, via a controller device including a processor, the controller device being configured to be in communication with the articulating arm member; and
directing the articulating arm member to at least maintain the patient-interacting device at a minimum vertical disposition, via the controller device, in response to disengagement between the patient-interacting device and the user determined by an engagement sensor operably engaged with the patient-interacting device and configured to be in communication with the controller device.

17. The method according to claim 16, further comprising directing the articulating arm member to maintain the patient-interacting device at one of a lateral disposition and a rotational orientation, in response to disengagement between the patient-interacting device and the user determined by the engagement sensor.

18. The method according to claim 16, further comprising actuating the articulating arm member to guide at least the instrument of the patient-interacting device, relative to the fiducial marker, in response to engagement between the patient-interacting device and the user determined by the engagement sensor.

19. The method according to claim 16, further comprising at least permitting the instrument to be actuated, in response to engagement between the patient-interacting device and the user determined by the engagement sensor.

20. The method according to claim 16, further comprising directing the controller device to actuate a virtual implantation plan for guiding at least the instrument of the patient-interacting device, in response to engagement between the patient-interacting device and the user determined by the engagement sensor.

21. The method according to claim 16, wherein directing the articulating arm member in response to disengagement between the patient-interacting device and the user determined by an engagement sensor operably engaged with the patient-interacting device, further comprises directing the articulating arm member in response to disengagement between the patient-interacting device and the user determined by one of a touch-sensitive actuator, a pressure-sensitive actuator, an optical actuator, and an acoustic actuator, associated with the patient-interacting device.

22. The method according to claim 16, further comprising communicating between the engagement sensor, and the controller device, via one of an electrical communication system, a mechanical communication system, an electromechanical communication system, an optical communication system, and combinations thereof.

23. The method according to claim 16, further comprising communicating between the engagement sensor, and the controller device, via one of wireless communication system and a wired communication system.

24. The method according to claim 16, further comprising measuring a force acting on the patient-interacting device, and communicating the measured force to the controller device, the measured force being determined by at least one force sensor operably engaged with at least one of the articulating arm member and the patient-interacting device.

25. The method according to claim 24, further comprising zeroing the measured force from the at least one force sensor, via the controller device, in response to disengagement from the engagement sensor by the user.

26. The method according to claim 16, further comprising executing a virtual implantation plan for the site within the mouth of the patient, and directing the articulating arm member according to the virtual implantation plan, via the controller device, in response to engagement of the engagement sensor by the user.

27. The method according to claim 26, further comprising directing tactile feedback to the user, via the patient-interacting device, if the instrument manipulated by the user deviates from the virtual implantation plan.

28. The method according to claim 26, further comprising directing at least one of audio feedback and visual feedback to the user, via at least one of the controller device and the patient-interacting device, if the instrument manipulated by the user deviates from the virtual implantation plan.

29. The method according to claim 16, further comprising displaying, via a display device, a real-time representation of at least the instrument of the patient-interacting device, in relation to a representation of the mouth of the patient, during engagement with and manipulation of the patient-interacting device by the user.

30. The method according to claim 29, further comprising monitoring manipulation of at least the instrument of the patient-interacting device in relation to the mouth of the patient, at least partially via the articulating arm member and the controller device, and directing information associated therewith to the display device.

31. A dental implantation system, comprising:
a patient-interacting device having an instrument adapted to at least interact with and prepare a site within a mouth of a patient for receiving a dental implant;
a guiding device comprising an articulating arm member in communication with a fiducial marker adapted to be engaged with the mouth of the patient, the articulating arm member being configured to receive the patient-interacting device at a distal end thereof, and to guide the instrument of the patient-interacting device, relative to the fiducial marker, in conjunction with manipulation of the patient-interacting device by a user;
a display device configured to display a real-time representation of the instrument of the patient-interacting device, in relation to a representation of the mouth of the patient, during manipulation of the patient-interacting device by the user; and
a controller device including a processor, and configured to be in communication with the articulating arm member and the display device, the controller device being configured to direct the patient-interacting device, via the articulating arm member and according to a virtual implantation plan, to prepare the site to receive the dental implant, and to direct tactile feedback to the user, via the patient-interacting device, if the instrument manipulated by the user deviates from the virtual implantation plan, the controller device being further configured to direct the display device to display the real-time representation of the instrument in relation to a virtual representation of the instrument of the patient-interacting device manipulated in accordance with the virtual implantation plan, and direct an audio device in communication therewith to emit a selected audio signal indicative of the instrument of the patient-interacting device in the real-time representation of the instrument being manipulated in accordance with the virtual implantation plan, or direct the articulating arm member to provide a selected resistance to manipulation of the instrument of the patient-interacting device in accordance with the real-time representation of the instrument in relation to the virtual implantation plan.

32. The system according to claim 31, wherein the controller device is further configured to direct the display device to display an animation of the virtual representation of the instrument of the patient-interacting device manipulated in accordance with the virtual implantation plan, the animation originating from a disposition of the real-time representation of the instrument of the patient-interacting device.

33. The system according to claim 32, wherein the controller device is further configured to direct the display device to display a progress indicia originating from the disposition of the real-time representation of the instrument of the patient-interacting device, and progressing in relation to a required manipulation of the patient-interacting device for the instrument to be in accordance with the virtual implantation plan.

34. The system according to claim 33, wherein the progress indicia comprises one of a distance originating from the disposition of the real-time representation of the instrument to a disposition of the instrument in accordance with the virtual implantation plan, and a degree of rotation originating from the disposition of the real-time representation of the instrument to a disposition of the instrument in accordance with the virtual implantation plan.

35. The system according to claim 31, wherein the audio device is configured to emit a selected audio signal, the selected audio signal increasing in frequency from the disposition of the real-time representation of the instrument toward a disposition of the instrument in accordance with the virtual implantation plan.

36. The system according to claim 31, wherein the articulating arm member is configured to provide a low resistance to manipulation of the patient-interacting device on one of manipulation of the patient-interacting device to move the instrument along a pathway in accordance with the virtual implantation plan, and manipulation of the patient-interacting device to rotate the instrument to a degree of rotation in accordance with the virtual implantation plan, the articulating arm member being further configured to provide a high resistance to manipulation of the patient-interacting device if one of the movement of the instrument along the pathway and rotation of the instrument deviates from the virtual implantation plan.

37. A dental implantation method, comprising:
guiding an instrument of a patient-interacting device, via a guiding device comprising an articulating arm member and relative to a fiducial marker adapted to be engaged with a mouth of a patient, in conjunction with manipulation of the patient-interacting device by a user, the patient-interacting device being received by a distal end of the articulating arm member, and the instrument being configured to interact with and prepare the site within the mouth of the patient for receiving a dental implant;
displaying a real-time representation of the instrument of the patient-interacting device on a display device, in relation to a representation of the mouth of the patient, during manipulation of the patient-interacting device by the user;
directing the patient-interacting device, via the articulating arm member and according to a dental implantation plan, to prepare the site to receive the dental implant, via a controller device including a processor, the controller device being configured to be in communication with the articulating arm member and the display device;
directing tactile feedback to the user, via the patient-interacting device, if the instrument manipulated by the user deviates from the virtual implantation plan; and
one of directing the display device, via the controller device, to display the real-time representation of the instrument in relation to a virtual representation of the instrument of the patient-interacting device manipulated in accordance with the virtual implantation plan; directing an audio device, via the controller device in communication therewith, to emit a selected audio signal indicative of the patient-interacting device manipulated in accordance with the virtual implantation plan; and directing the articulating arm member, via the controller device, to provide a selected resistance to manipulation of the patient-interacting device in accordance with the virtual implantation plan.

38. The method according to claim 37, wherein directing the display device, via the controller device, to display the real-time representation of the instrument, further comprises directing the display device, via the controller device, to display an animation of the virtual representation of the instrument of the patient-interacting device manipulated in accordance with the virtual implantation plan, the animation originating from a disposition of the real-time representation of the instrument of the patient-interacting device.

39. The method according to claim 38, further comprising directing the display device, via the controller device, to display a progress indicia originating from the disposition of the real-time representation of the instrument of the patient-interacting device, and progressing in relation to a required manipulation of the patient-interacting device for the instrument to be in accordance with the virtual implantation plan.

40. The method according to claim 39, wherein directing the display device, via the controller device, to display a progress indicia, further comprises, directing the display device, via the controller device, to display a progress indicia comprising one of a distance originating from the disposition of the real-time representation of the instrument to a disposition of the instrument in accordance with the virtual implantation plan, and a degree of rotation originating from the disposition of the real-time representation of the instrument to a disposition of the instrument in accordance with the virtual implantation plan.

41. The method according to claim 37, wherein directing an audio device, via the controller device in communication therewith, to emit a selected audio signal, further comprises directing an audio device, via the controller device in communication therewith, to emit a selected audio signal increasing in frequency from the disposition of the real-time representation of the instrument toward a disposition of the instrument in accordance with the virtual implantation plan.

42. The method according to claim 37, wherein directing the articulating arm member, via the controller device, to provide a selected resistance to manipulation of the patient-interacting device, further comprises directing the articulating arm member, via the controller device, to provide a low resistance to manipulation of the patient-interacting device on one of manipulation of the patient-interacting device to move the instrument along a pathway in accordance with the virtual implantation plan, and manipulation of the patient-interacting device to rotate the instrument to a degree of rotation in accordance with the virtual implantation plan, and directing the articulating arm member, via the controller device, to provide a high resistance to manipulation of the patient-interacting device if one of the movement of the instrument along the pathway and rotation of the instrument deviates from the virtual implantation plan.

* * * * *